United States Patent
Nakai et al.

(10) Patent No.: US 12,064,513 B2
(45) Date of Patent: Aug. 20, 2024

(54) CATIONIC LIPID EXHIBITING IMPROVED INTRACELLULAR DYNAMICS

(71) Applicants: NOF CORPORATION, Tokyo (JP); NATIONAL UNIVERSITY CORPORATION CHIBA UNIVERSITY, Chiba (JP)

(72) Inventors: Yuta Nakai, Kawasaki (JP); Kota Tange, Kawasaki (JP); Hiroki Yoshioka, Kawasaki (JP); Shinya Tamagawa, Kawasaki (JP); Hidetaka Akita, Chiba (JP); Hiroki Tanaka, Chiba (JP); Nae Takata, Chiba (JP); Manami Konishi, Chiba (JP); Tatsunari Takahashi, Chiba (JP)

(73) Assignees: NOF CORPORATION, Tokyo (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 326 days.

(21) Appl. No.: 17/040,960

(22) PCT Filed: Mar. 25, 2019

(86) PCT No.: PCT/JP2019/012302
§ 371 (c)(1),
(2) Date: Sep. 23, 2020

(87) PCT Pub. No.: WO2019/188867
PCT Pub. Date: Oct. 3, 2019

(65) Prior Publication Data
US 2021/0023008 A1    Jan. 28, 2021

(30) Foreign Application Priority Data
Mar. 27, 2018   (JP) .................... 2018-060764

(51) Int. Cl.
| | | |
|---|---|---|
| A61K 9/127 | (2006.01) |
| A61K 47/22 | (2006.01) |
| A61K 48/00 | (2006.01) |
| C07C 323/25 | (2006.01) |
| C07D 211/22 | (2006.01) |
| C07D 405/14 | (2006.01) |

(52) U.S. Cl.
CPC ............ *A61K 9/1272* (2013.01); *A61K 47/22* (2013.01); *A61K 48/00* (2013.01); *C07C 323/25* (2013.01); *C07D 211/22* (2013.01); *C07D 405/14* (2013.01)

(58) Field of Classification Search
CPC ...... A61K 9/1272; A61K 47/22; A61K 48/00; C07C 323/25; C07D 211/22; C07D 405/14
USPC .......................................................... 564/1
See application file for complete search history.

(56) References Cited

U.S. PATENT DOCUMENTS

| | | |
|---|---|---|
| 6,124,270 A | 9/2000 | Haensler |
| 6,927,213 B2 | 8/2005 | Deshmukh et al. |
| 9,708,628 B2 | 7/2017 | Tange et al. |
| 2002/0142029 A1 | 10/2002 | Porta et al. |
| 2006/0029655 A1 | 2/2006 | Barenholz et al. |
| 2010/0055684 A1 | 3/2010 | Kikuchi et al. |
| 2013/0123338 A1 | 5/2013 | Heyes et al. |
| 2014/0316006 A1 | 10/2014 | Greaves et al. |

(Continued)

FOREIGN PATENT DOCUMENTS

| | | |
|---|---|---|
| JP | 2011-121966 A | 6/2011 |
| JP | 2011-172519 A | 9/2011 |

(Continued)

OTHER PUBLICATIONS

Akita et al., "A Neutral Envelope-Type Nanoparticle Containing pH-Responsive and SS-Cleavable Lipid-Like Material as a Carrier for Plasmid DNA," *Adv. Healthc. Mater.*, 2(8): 1120-1125 (2013).
Alabi et al., "Multiparametric approach for the evaluation of lipid nanoparticles for siRNA delivery," *Proc. Natl. Acad. Sci. U.S.A.*, 110(32): 12881-12886 (2013).
Hama et al., "Quantitative Comparison of Intracellular Trafficking and Nuclear Transcription between Adenoviral and Lipoplex Systems," *Mol. Ther.*, 13(4): 786-794 (2006).
Jayaraman et al., "Maximizing the Potency of siRNA Lipid Nanoparticles for Hepatic Gene Silencing In Vivo," *Angew. Chem. Int. Ed. Engl.*, 51(34): 8529-8533 (2012).
Sato et al., "Relationship Between the Physicochemical Properties of Lipid Nanoparticles and the Quality of siRNA Delivery to Liver Cells," *Mol. Ther.*, 24(4): 788-795 (2016).
Tanaka et al., "Neutral biodegradable lipid-envelope-type nanoparticle using vitamin A-Scaffold for nuclear targeting of plasmid DNA," *Biomaterials*, 35(5): 1755-1761 (2014).

(Continued)

*Primary Examiner* — Ana Z Muresan
(74) *Attorney, Agent, or Firm* — Leydig, Voit & Mayer, Ltd.

(57) ABSTRACT

The invention provides a cationic lipid, a lipid membrane structure containing same, and use thereof. The cationic lipid is represented by the formula (1)

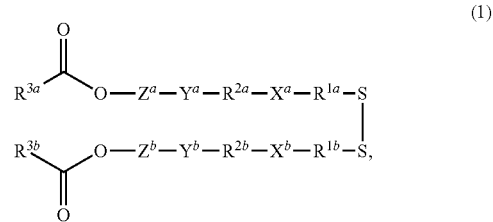

(1)

wherein $R^{1a}$, $R^{1b}$, $R^{2a}$, $R^{2b}$, $R^{3a}$, $R^{3b}$, $X^a$, $X^b$, $Y^a$, $Y^b$, $Z^a$, and $Z^b$ are as defined in the specification.

17 Claims, 6 Drawing Sheets

(56) References Cited

U.S. PATENT DOCUMENTS

| | | |
|---|---|---|
| 2014/0335157 A1 | 11/2014 | Tange et al. |
| 2018/0155304 A1 | 6/2018 | Nakai et al. |
| 2018/0298379 A1 | 10/2018 | Yang et al. |
| 2021/0023008 A1 | 1/2021 | Nakai et al. |
| 2022/0192981 A1 | 6/2022 | Nakai et al. |

FOREIGN PATENT DOCUMENTS

| | | | |
|---|---|---|---|
| RU | 2233834 C2 | 8/2004 | |
| WO | WO 2000/027795 A1 | 5/2000 | |
| WO | WO 2005/120152 A2 | 12/2005 | |
| WO | WO 2011/115862 A1 | 9/2011 | |
| WO | WO 2012/040184 A2 | 3/2012 | |
| WO | WO-2012091523 A2 * | 7/2012 | ........... A61K 31/713 |
| WO | WO 2013/050547 A1 | 4/2013 | |
| WO | WO2016121942 * | 8/2016 | |
| WO | WO 2017/049245 A2 | 3/2017 | |
| WO | WO2017/061150 * | 4/2017 | |
| WO | WO 2017/218704 A1 | 12/2017 | |

OTHER PUBLICATIONS

Japanese Patent Office, International Search Report in International Patent Application No. PCT/JP2019/012302 (Jun. 18, 2019).

Shirane et al., "Development of an Alcohol Dilution-Lyophilization Method for Preparing Lipid Nanoparticles Containing Encapsulated siRNA," *Biol. Pharm. Bull.*, 41(8): 1291-1294 and Supplementary Materials (2018).

Wheeler et al., "Stabilized plasmid-lipid particles: construction and characterization," *Gene Therapy*, 6(2): 271-281 (1999).

Heyes et al., "Cationic lipid saturation influences intracellular delivery of encapsulated nucleic acids," *Journal of Controlled Release*, 107: 276-287 (2005).

Morille et al., "Progress in developing cationic systems for non-viral vector systemic gene therapy against cancer," *Biomaterials*, 29(24-25): 3477-3496 (2008).

Semple et al., "Rational design of cationic lipids for siRNA delivery," *Nature Biotechnology*, 28: 172-176 (2010).

Weissbuch et al., "Structure and dynamics of amphiphilic aggregates at air/solution interfaces en route to crystal formation," *Pure & Appl. Chem.*, 64(9): 1263-1270 (1992).

* cited by examiner

CATIONIC LIPID EXHIBITING IMPROVED INTRACELLULAR DYNAMICS

CROSS-REFERENCE TO RELATED APPLICATIONS

This patent application is the U.S. national phase of International Patent Application No. PCT/JP2019/012302, filed on Mar. 25, 2019, which claims the benefit of Japanese Patent Application No. 2018-060764 filed on Mar. 27, 2018, which are incorporated by reference in their entireties herein.

TECHNICAL FIELD

The present invention relates to a cationic lipid having improved intracellular kinetics, a lipid membrane structure containing same, and use thereof.

BACKGROUND ART

For practicalization of nucleic acid therapy, an effective and safe nucleic acid delivery carrier is demanded. While virus vectors are nucleic acid delivery carriers with good expression efficiency, they have practical problems from the aspect of safety. Therefore, the development of non-viral nucleic acid delivery carriers that can be used more safely is ongoing. Among them, carriers using a cationic lipid are non-viral nucleic acid delivery carriers most generally used at present.

Cationic lipids are largely composed of an amine moiety and a lipid moiety, wherein the amine moiety showing cationicity and a polyanion nucleic acid electrostatically interact to form a positively-charged liposome or lipid membrane structure, which promotes uptake into cells and delivers the nucleic acid into cells.

As known cationic lipids generally and widely used, DOTAP and DODAP can be mentioned. These known cationic lipids form a positively-charged liposome or lipid membrane structure when combined with a phospholipid, which electrostatically interacts with a nucleic acid to be able to deliver the nucleic acid to the target cells (non-patent document 1).

On the other hand, for a lipid membrane structure using a cationic lipid to exhibit a practical effect in vivo as a nucleic acid delivery carrier, the requirements of good pharmacokinetics, specifically high stability in blood, property to highly accumulate in the target such as tumor, and the like need to be fulfilled. Given the problem, it is known that a lipid membrane structure introduced with PEG lipid and having a surface pKa adjusted to around neutral shows a long lifetime in blood after intravenous injection, and accumulates in tumor sites.

While cationic lipids having improved pharmacokinetics have been developed as shown above, in view of the property of the nucleic acid delivery carriers that they generally introduce exogenous substances into cells, a large effect output from a small uptake amount is desired. That is, when a lipid membrane structure is used as a delivery carrier of an expression vector into cells, it is desired to increase the expression level per unit lipid membrane structure incorporated into the cells and enhance intracellular expression efficiency. To enhance the intracellular expression efficiency, it is necessary to also improve, besides pharmacokinetics, intracellular kinetics such as uptake process into cells, escape from endosome, nuclear membrane permeation and the like. Moreover, it is known that dissociation of nucleic acids from the carrier and enhancement of the bindability of transcription factors are necessary to facilitate intracellular transcription (non-patent document 2).

As described above, a carrier for nucleic acid delivery requires improvement of not only pharmacokinetics but also intracellular dynamics. Particularly, it is important to promote uptake into cells, endosomal escape, and dissociation of nucleic acid from carrier. The following reports improvement examples of these intracellular dynamics.

Patent document 1 describes an example in which the amount of uptake into cells was increased. The document describes a cationic lipid containing a large amount of amino group so as to increase the amount of uptake into cells. A lipid membrane structure containing the cationic lipid can increase the amount of uptake into cells, whereas improvement in nucleic acid delivery efficiency cannot be expected, since the lipid membrane structure has many amino groups that interact with nucleic acid, and the dissociation of nucleic acid from the lipid membrane structure is suppressed in cells.

There are examples of improved endosomal escape efficiency (non-patent document 3 and non-patent document 4). In these documents, the structure around the amino group of the cationic lipid was modified, and the pKa on the surface of the lipid membrane structure was adjusted to a value preferable for endosomal escape. As a result, it is stated that the escape of the lipid membrane structure from the endosome is promoted, and the nucleic acid can be efficiently delivered into the cytoplasm. However, not all lipid membrane structures with an appropriate pKa show high nucleic acid delivery efficiency, and there is no description about the effects of the cationic lipids in these documents which are other than the adjustment of pKa of the lipid membrane structure.

Improving the membrane fusion capacity of a lipid membrane structure is also one of the methods for improving the endosomal escape efficiency (non-patent document 5). In this document, the membrane fusion capacity (hemolysis activity) was evaluated as one index of endosomal escape ability. It is described that the membrane fusion capacity changes by modifying the structure of the cationic lipids that constitute the lipid membrane structure, and the membrane fusion capacity in the endosomal environment affects the nucleic acid delivery efficiency. However, what structure improves the membrane fusion capacity is not described.

There are examples in which intracellular dissociation of nucleic acid from a lipid membrane structure was promoted (patent documents 2 and 3). These documents describe a cationic lipid having a structure in which compounds composed of one or two amine moieties and one lipid moiety are linked to each other by a biodegradable disulfide bond. These documents show that the cationic lipid can improve pharmacokinetics such as stability in blood, tumor targeting property and the like, pKa of a lipid membrane structure can be adjusted to a value favorable for intracellular endosomal escape by changing the structure around the amine moiety, and further that it has an effect of dissociating nucleic acid from a lipid membrane structure by utilizing intracellular cleavage of a disulfide bond. In fact, it has been clarified that the cationic lipid can improve intracellular dynamics such as improvement of delivery efficiency of nucleic acid into the cytoplasm and the like, since it shows high nucleic acid delivery efficiency as compared to known cationic lipids, DOTAP and DODAP.

As described above, there are plural reports relating to the improvement of intracellular dynamics of a carrier for nucleic acid delivery, such as promotion of uptake into cells, endosomal escape, and dissociation of nucleic acid from carrier. However, despite such technical progress in the pertinent field, the efficiency of nucleic acid delivery to cells which is achieved by the lipid membrane structure using these cationic lipids is not sufficiently satisfactory, and further improvement is desired.

DOCUMENT LIST

Patent Documents patent document 1: JP-A-2011-121966
patent document 2: US2014/0335157A1
patent document 3: WO 2016/121942

Non-Patent Documents non-patent document 1: Biomaterials 29(24-25):3477-96, 2008
non-patent document 2: Molecular Therapy 13(4):786-794, 2006
non-patent document 3: Molecular Therapy 24(4):788-795, 2016
non-patent document 4: Angewante Chemie International Edition 51:8529-8533, 2012
non-patent document 5: Proceedings of the National Academy of Science 110(32):12881-12886, 2013

SUMMARY OF INVENTION

Technical Problem

The problem of the present invention is to provide a cationic lipid that achieves further improvement of intracellular dynamics, which could not be achieved by the prior art, and can be used as a carrier for nucleic acid delivery, a lipid membrane structure using the cationic lipid, and a nucleic acid-introducing agent using the cationic lipid.

In addition, the problem of the present invention is to provide a method for achieving introduction of a nucleic acid by using a nucleic acid-introducing agent containing a cationic lipid.

Solution to Problem

In view of the above-mentioned problems, the present inventors have conducted intensive studies and found a cationic lipid that can adjust pKa of a lipid membrane structure that influences endosomal escape efficiency, and that has high membrane fusion capacity. Specifically, it is a cationic lipid having a structure in which compounds obtained by introducing an aromatic ring into the vicinity of a lipid moiety and binding same to an amine moiety are linked by a disulfide bond. Since the cationic lipid has a disulfide bond, the disulfide bond is cleaved in the cell, thus also affording an effect of dissociating nucleic acid from the lipid membrane structure.

They have found that a lipid membrane structure containing the novel cationic lipid shows high membrane fusion capacity in the endosomal environment, shows high endosomal escape efficiency, and thus can deliver nucleic acid efficiently into the cytoplasm.

Accordingly, the present invention encompasses the following.

[1] A cationic lipid represented by the formula (1)

$$R^{3a}\underset{O}{\overset{O}{\|}}O-Z^a-Y^a-R^{2a}-X^a-R^{1a}-S$$
$$R^{3b}\underset{O}{\overset{O}{\|}}O-Z^b-Y^b-R^{2b}-X^b-R^{1b}-S$$

(1)

(in the formula (1),
$R^{1a}$ and $R^{1b}$ are each independently an alkylene group having 1-6 carbon atoms,
$X^a$ and $X^b$ are each independently a non-cyclic alkyl tertiary amino group having 1-6 carbon atoms and one tertiary amino group, or a cyclic alkylene tertiary amino group having 2-5 carbon atoms and 1-2 tertiary amino groups,
$R^{2a}$ and $R^{2b}$ are each independently an alkylene group or an oxydialkylene group each having not more than 8 carbon atoms,
$Y^a$ and $Y^b$ are each independently an ester bond, an amide bond, a carbamate bond, an ether bond or a urea bond,
$Z^a$ and $Z^b$ are each independently a divalent group derived from an aromatic compound having 3-16 carbon atoms and at least one aromatic ring, and optionally having a hetero atom, and
$R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12-22 carbon atoms) (sometimes to be abbreviated as "cationic lipid (1)" in the present specification).

[2] The cationic lipid of [1], wherein $Z^a$ and $Z^b$ are each independently $Z^1$:

$$Z^1 = \left\{ ({-})_s \underset{}{\bigcirc}(R^4)_u ({-})_t \right\}$$

wherein
s is an integer of 0-3,
t is an integer of 0-3,
u is an integer of 0-4
$R^4$ in the number of u are each independently a substituent.

[3] The cationic lipid of [2], wherein s is 0.
[4] The cationic lipid of any one of [1] to [3], wherein $X^a$ and $X^b$ are each independently a cyclic alkylene tertiary amino group having 2-5 carbon atoms and 1-2 tertiary amino groups.
[5] The cationic lipid of any one of [1] to [4], wherein $R^{3a}$ and $R^{3b}$ are each independently a residue derived from a reaction product of a liposoluble vitamin having a hydroxyl group, and succinic anhydride or glutaric anhydride, or an aliphatic hydrocarbon group having 12-22 carbon atoms.

[6] The cationic lipid of [5], wherein $R^{3a}$ and $R^{3b}$ are each independently a residue derived from a reaction product of a liposoluble vitamin having a hydroxyl group, and succinic anhydride or glutaric anhydride.

[7] The cationic lipid of [5], wherein $R^{3a}$ and $R^{3b}$ are each independently an aliphatic hydrocarbon group having 12-22 carbon atoms.

[8] A lipid membrane structure comprising the cationic lipid of any one of [1] to [7] as a constituent lipid of the membrane.

[9] A nucleic acid-introducing agent, comprising the cationic lipid of any one of [1] to [7], or the lipid membrane structure of [8].

[10] A method for introducing a nucleic acid into a cell in vitro, comprising bringing the nucleic acid-introducing agent of [9] encapsulating the nucleic acid into contact with the cell.

[11] A method for introducing a nucleic acid into a target cell, comprising administering the nucleic acid-introducing agent of [9] encapsulating the nucleic acid to a living organism to allow for delivery of the nucleic acid to the cell.

Advantageous Effects of Invention the present invention relates to a cationic lipid containing an ester having a tertiary amino group and an aromatic ring, a lipid moiety, and a disulfide bond which is a biodegradable group, and a lipid membrane structure containing the cationic lipid. The cationic lipid of the present invention can form a lipid membrane structure, and can provide a nucleic acid-introducing agent containing the cationic lipid. The cationic lipid of the present invention can adjust pKa of a lipid membrane structure that influences endosomal escape efficiency, also has high membrane fusion capacity in the endosomal environment, and thus promotes endosomal escape. Furthermore, the disulfide bond contained in the cationic lipid of the present invention is cleaved in the intracellular reductive environment and release of an encapsulated material (nucleic acid) is promoted. Hence, a nucleic acid-introducing agent using the cationic lipid of the present invention can achieve high efficiency of nucleic acid delivery into the cytoplasm.

When nucleic acid is introduced using the cationic lipid of the present invention, or a lipid membrane structure containing the same, degradation of the nucleic acid by the serum components is suppressed, which is advantageous for nucleic acid introduction in the presence of serum or nucleic acid introduction in vivo.

DESCRIPTION OF EMBODIMENTS

Figure 1:
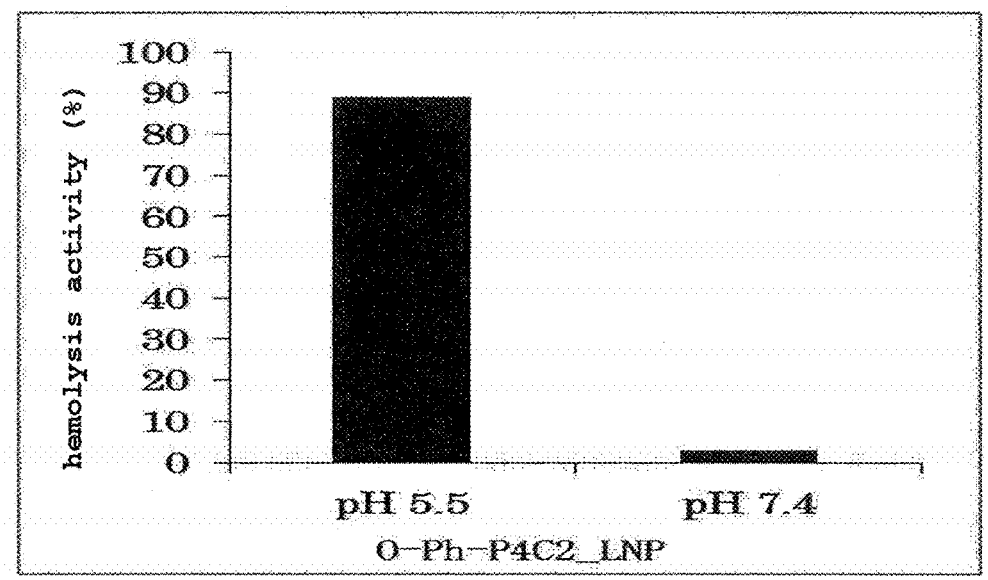
FIG. 1 shows the hemolysis activity (membrane fusion capacity) at pH 7.4 and pH 5.5 of LNP prepared from the cationic lipid of the present invention (O-Ph-P4C2).

While the embodiments of the present invention are explained in the following, the present invention is not limited thereto.

The present invention provides a cationic lipid represented by the formula (1).

$R^{1a}$ and $R^{1b}$ are each independently an alkylene group having 1-6 carbon atoms, and may be linear or branched, preferably linear. The carbon number of the alkylene group is preferably 1-4, more preferably 1-2. Specific examples of the alkylene group having 1-6 carbon atoms include methylene group, ethylene group, trimethylene group, isopropylene group, tetramethylene group, isobutylene group, pentamethylene group, neopentylene group and the like. Preferably, $R^{1a}$ and $R^{1b}$ are each independently a methylene group, an ethylene group, a trimethylene group, an isopropylene group or a tetramethylene group, most preferably an ethylene group.

$R^{1a}$ may be the same as or different from $R^{1b}$, and $R^{1a}$ is preferably the same group as $R^{1b}$.

$X^a$ and $X^b$ are each independently a non-cyclic alkyl tertiary amino group having 1-6 carbon atoms and one tertiary amino group, or a cyclic alkylene tertiary amino group having 2-5 carbon atoms and 1-2 tertiary amino groups, preferably each independently a cyclic alkylene tertiary amino group having 2-5 carbon atoms and 1-2 tertiary amino groups.

The alkyl group having 1-6 carbon atoms in the non-cyclic alkyl tertiary amino group having 1-6 carbon atoms and one tertiary amino group may be linear, branched or cyclic. The alkyl group preferably has a carbon number of 1-3. Specific examples of the alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like, preferably methyl group, ethyl group, propyl group or isopropyl group, most preferably methyl group.

A preferable specific structure of the non-cyclic alkyl tertiary amino group having 1-6 carbon atoms and one tertiary amino group is represented by $X^1$.

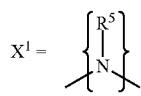

$R^5$ in $X^1$ is an alkyl group having 1-6 carbon atoms, which may be linear, branched or cyclic. The alkyl group preferably has a carbon number of 1-3. Specific examples of the alkyl group having 1-6 carbon atoms include methyl group, an ethyl group, a propyl group, an isopropyl group, n-butyl group, a sec-butyl group, an isobutyl group, a tert-butyl group, a pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. $R^5$ is preferably a methyl group, an ethyl group, a propyl group or an isopropyl group, most preferably a methyl group.

The carbon number of the cyclic alkylene tertiary amino group having 2-5 carbon atoms and 1-2 tertiary amino groups is preferably 4-5. The cyclic alkylene tertiary amino group having 2-5 carbon atoms and 1-2 tertiary amino groups is specifically aziridylene group, azetidylene group, pyrrolidylene group, piperidylene group, imidazolidylene group, or piperazylene group, preferably pyrrolidylene group, piperidylene group, or piperazylene group, most preferably piperidylene group.

A preferable specific structure of the cyclic alkylene tertiary amino group having 2-5 carbon atoms and one tertiary amino group is represented by $X^2$.

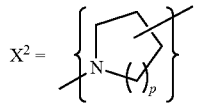

The p of $X^2$ is 1 or 2. When p is 1, $X^2$ is a pyrrolidylene group, and when p is 2, $X^2$ is a piperidylene group.

A preferable specific structure of the cyclic alkylene tertiary amino group having 2-5 carbon atoms and two tertiary amino groups is represented by $X^3$.

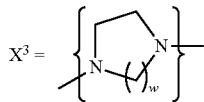

The w of $X^3$ is 1 or 2. When w is 1, $X^3$ is an imidazolidylene group, and when w is 2, $X^3$ is a piperazylene group.

$X^a$ may be the same as or different from $X^b$, and $X^a$ is preferably the same group as $X^b$.

$R^{2a}$ and $R^{2b}$ are each independently an alkylene group or an oxydialkylene group each having not more than 8 carbon atoms, preferably each independently an alkylene group having not more than 8 carbon atoms.

The alkylene group having not more than 8 carbon atoms may be linear or branched, preferably linear. The number of carbons contained in the alkylene group is preferably not more than 6, most preferably not more than 4. Specific examples of the alkylene group having not more than 8 carbon atoms include methylene group, ethylene group, propylene group, isopropylene group, tetramethylene group, isobutylene group, pentamethylene group, hexamethylene group, heptamethylene group, octamethylene group and the like, preferably methylene group, ethylene group, propylene group, and tetramethylene group, most preferably ethylene group.

The oxydialkylene group having not more than 8 carbon atoms contains alkylene groups via an ether bond (alkylene-O-alkylene), wherein the total carbon number of the two alkylene groups present is 8 or below. The two alkylene groups present may be the same or different, preferably the same. Specific examples of the oxydialkylene group having not more than 8 carbon atoms include oxydimethylene group, oxydiethylene group, oxydipropylene group, oxydibutylene group and the like. Preferably, it is oxydimethylene group, oxydiethylene group, or oxydipropylene group, most preferably oxydiethylene group.

$R^{2a}$ may be the same as or different from $R^{2b}$, and $R^{2a}$ is preferably the same group as $R^{2b}$.

$Y^a$ and $Y^b$ are each independently an ester bond, an amide bond, a carbamate bond, an ether bond or a urea bond, preferably each independently an ester bond, an amide bond or a carbamate bond, more preferably each independently an ester bond or an amide bond, most preferably each an ester bond. The direction of the bond of $Y^a$ and $Y^b$ is not limited. When $Y^a$ and $Y^b$ are ester bonds, the structure of —$Z^a$—CO—O—$R^{2a}$— or —$Z^b$—CO—O—$R^{2b}$— is preferably shown.

$Y^a$ may be the same as or different from $Y^b$, and $Y^a$ is preferably the same group as $Y^b$.

$Z^a$ and $Z^b$ are each independently a divalent group derived from an aromatic compound having 3-16 carbon atoms and at least one aromatic ring, and optionally having a hetero atom. The number of carbons contained in the aromatic compound is preferably 6-12, most preferably 6-7. The aromatic ring contained in the aromatic compound is preferably one.

As the kind of the aromatic ring contained in the aromatic compound having 3-16 carbon atoms, benzene ring, naphthalene ring, and anthracene ring can be mentioned for aromatic hydrocarbocycle, and imidazole ring, a pyrazole ring, oxazole ring, an isoxazole ring, thiazole ring, isothiazole ring, triazine ring, a pyrrole ring, furanthiophene ring, a pyrimidine ring, a pyridazine ring, a pyrazine ring, a pyridine ring, purine ring, pteridine ring, benzimidazole ring, indole ring, benzofuran ring, quinazoline ring, phthalazine ring, quinoline ring, isoquinoline ring, coumarin ring, chromone ring, benzodiazepine ring, phenoxazine ring, phenothiazine ring, acridine ring and the like can be mentioned for aromatic heterocycle. It is preferably benzene ring, naphthalene ring, or anthracene ring, most preferably benzene ring.

The aromatic ring may have a substituent. Examples of the substituent include acyl group having 2-4 carbon atoms, alkoxycarbonyl group having 2-4 carbon atoms, carbamoyl group having 2-4 carbon atoms, acyloxy group having 2-4 carbon atoms, acylamino group having 2-4 carbon atoms, alkoxycarbonylamino group having 2-4 carbon atoms, fluorine atom, chlorine atom, bromine atom, iodine atom, alkylsulfanyl group having 1-4 carbon atoms, alkylsulfonyl group having 1-4 carbon atoms, arylsulfonyl group having 6-10 carbon atoms, nitro group, trifluoromethyl group, a cyano group, alkyl group having 1-4 carbon atoms, ureido group having 1-4 carbon atoms, alkoxy group having 1-4 carbon atoms, aryl group having 6-10 carbon atoms, aryloxy group having 6-10 carbon atoms, and the like. Preferable examples include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, t-butyl group, ureido group, methoxy group, ethoxy group, propoxy group, isopropoxy group, t-butoxy group, phenyl group, phenoxy group and the like.

A preferable specific structure of $Z^a$ and $Z^b$ is $Z^1$.

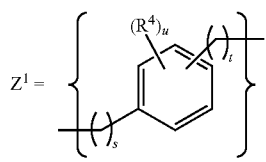

wherein s is an integer of 0-3, t is an integer of 0-3, u is an integer of 0-4, and $R^4$ in the number of u are each independently a substituent.

The s for $Z^1$ is preferably an integer of 0-1, more preferably 0.

The t for $Z^1$ is preferably an integer of 0-2, more preferably 1.

The u for $Z^1$ is preferably an integer of 0-2, more preferably an integer of 0-1.

The $R^4$ for $Z^1$ is a substituent of an aromatic ring (benzene ring) contained in the aromatic compound having 3-16 carbon atoms which does not inhibit the reaction in the synthesis process of a cationic lipid. Examples of the substituent include acyl group having 2-4 carbon atoms, alkoxycarbonyl group having 2-4 carbon atoms, carbamoyl group having 2-4 carbon atoms, acyloxy group having 2-4 carbon atoms, acylamino group having 2-4 carbon atoms, alkoxycarbonylamino group having 2-4 carbon atoms, fluorine atom, chlorine atom, bromine atom, iodine atom, alkylsulfanyl group having 1-4 carbon atoms, alkylsulfonyl group having 1-4 carbon atoms, arylsulfonyl group having 6-10 carbon atoms, nitro group, trifluoromethyl group, a cyano group, alkyl group having 1-4 carbon atoms, ureido group having 1-4 carbon atoms, alkoxy group having 1-4 carbon atoms, aryl group having 6-10 carbon atoms, aryloxy group having 6-10 carbon atoms, and the like. Preferable examples include acetyl group, methoxycarbonyl group, methylcarbamoyl group, acetoxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, t-butyl group, ureido group, methoxy group, ethoxy group, propoxy group, isopropoxy group, t-butoxy group, phenyl group, phenoxy group and the like. When $R^4$ is present in plurality, each $R^4$ may be the same or different.

$Z^a$ may be the same as or different from $Z^b$, and $Z^a$ is preferably the same group as $Z^b$.

$R^{3a}$ and $R^{3b}$ are each independently a residue derived from a reaction product of a liposoluble vitamin having a hydroxyl group, and succinic anhydride or glutaric anhydride, or a residue derived from a reaction product of a sterol derivative having a hydroxyl group, and succinic anhydride or glutaric anhydride, or an aliphatic hydrocarbon group having 12-22 carbon atoms, preferably each independently a residue derived from a reaction product of a liposoluble vitamin having a hydroxyl group, and succinic anhydride or glutaric anhydride, or an aliphatic hydrocarbon group having 12-22 carbon atoms, most preferably each independently an aliphatic hydrocarbon group having 12-22 carbon atoms.

The liposoluble vitamin having a hydroxyl group is, for example, retinol, ergosterol, 7-dehydrocholesterol, calciferol, cholecalciferol, dihydroergocalciferol, dihydrotachysterol, tocopherol, tocotrienol and the like. Preferred example of the liposoluble vitamin having a hydroxyl group is tocopherol.

Examples of the sterol derivative having a hydroxyl group include cholesterol, cholestanol, stigmasterol, β-sitosterol, lanosterol, and ergosterol and the like, preferably cholesterol or cholestanol.

The aliphatic hydrocarbon group having 12-22 carbon atoms may be linear or branched. The aliphatic hydrocarbon group may be saturated or unsaturated. In the case of an unsaturated aliphatic hydrocarbon group, the aliphatic hydrocarbon group generally contains 1-6, preferably 1-3, more preferably 1-2 unsaturated bonds. While the unsaturated bond includes a carbon-carbon double bond and a carbon-carbon triple bond, it is preferably a carbon-carbon double bond. The aliphatic hydrocarbon group has a carbon number of preferably 13-19, most preferably 13-17. While the aliphatic hydrocarbon group includes an alkyl group, an alkenyl group, an alkynyl group and the like, it is preferably an alkyl group or an alkenyl group. Specific examples of the aliphatic hydrocarbon group having 12-22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group and the like. The aliphatic hydrocarbon group having 12-22 carbon atoms is preferably tridecyl group, pentadecyl group, heptadecyl group, nonadecyl group, heptadecenyl group, heptadecadienyl group, or 1-hexylnonyl group, particularly preferably tridecyl group, heptadecyl group, heptadecenyl group, or heptadecadienyl group.

In one embodiment of the present invention, the aliphatic hydrocarbon group having 12-22 carbon atoms for $R^{3a}$ or $R^{3b}$ is derived from fatty acid. In this case, the carbonyl carbon derived from fatty acid is contained in —CO—O— in the formula (1). A specific example of the aliphatic hydrocarbon group is a heptadecadienyl group when linoleic acid is used as the fatty acid, and heptadecenyl group when oleic acid is used as the fatty acid.

$R^{3a}$ may be the same as or different from $R^{3b}$, and $R^{3a}$ is preferably the same group as $R^{3b}$.

In one embodiment of the present invention, $R^{1a}$ is the same as $R^{1b}$, $X^a$ is the same as $X^b$, $R^{2a}$ is the same as $R^{2b}$, $Y^a$ is the same as $Y^b$, $Z^a$ is the same as $Z^b$, and $R^{1a}$ is the same as $R^{3b}$.

Preferable examples of the cationic lipid represented by the formula (1) in the present invention include the following cationic lipids.

[Cationic Lipid (1-1)]
Cationic lipid (1) wherein
$R^{1a}$ and $R^{1b}$ are each independently an alkylene group having 1-6 carbon atoms (e.g., methylene group, ethylene group);
$X^a$ and $X^b$ are each independently a non-cyclic alkyl tertiary amino group having 1-6 carbon atoms and one tertiary amino group (e.g., —N(CH$_3$)—), or a cyclic alkylene tertiary amino group having 2-5 carbon atoms and 1-2 tertiary amino groups (e.g., piperidylene group);
$R^{2a}$ and $R^{2b}$ are each independently an alkylene group having not more than 8 carbon atoms (e.g., methylene group, ethylene group, propylene group);
$Y^a$ and $Y^b$ are each independently an ester bond or an amide bond;
$Z^a$ and $Z^b$ are each independently a divalent group derived from an aromatic compound having 3-16 carbon atoms and at least one aromatic ring, and optionally having a hetero atom (e.g., —C$_6$H$_4$—CH$_2$—, —CH$_2$—C$_6$H$_4$—CH$_2$—); and
$R^{3a}$ and $R^{3b}$ are each independently a residue derived from a reaction product of a liposoluble vitamin having a hydroxyl group (e.g., tocopherol), and succinic anhydride or glutaric anhydride, or an aliphatic hydrocarbon group having 12-22 carbon atoms (e.g., heptadecenyl group, heptadecadienyl group, 1-hexylnonyl group).

[Cationic Lipid (1-2)]
Cationic lipid (1) wherein
$R^{1a}$ and $R^{1b}$ are each independently an alkylene group having 1-4 carbon atoms (e.g., methylene group, ethylene group);
$X^a$ and $X^b$ are each independently a non-cyclic alkyl tertiary amino group having 1-3 carbon atoms and one tertiary amino group (e.g., —N(CH$_3$)—), or a cyclic alkylene tertiary amino group having 2-5 carbon atoms and one tertiary amino group (e.g., piperidylene group);
$R^{2a}$ and $R^{2b}$ are each independently an alkylene group having not more than 6 carbon atoms (e.g., methylene group, ethylene group, propylene group);
$Y^a$ and $Y^b$ are each independently an ester bond or an amide bond;
$Z^a$ and $Z^b$ are each independently a divalent group derived from an aromatic compound having 6-12 carbon atoms and one aromatic ring, and optionally having a hetero atom (e.g., —C$_6$H$_4$—CH$_2$—, —CH$_2$—C$_6$H$_4$—CH$_2$—); and
$R^{3a}$ and $R^{3b}$ are each independently a residue derived from a reaction product of a liposoluble vitamin having a hydroxyl group (e.g., tocopherol), and succinic anhydride, or an aliphatic hydrocarbon group having 13-19 carbon atoms (e.g., heptadecenyl group, heptadecadienyl group, 1-hexylnonyl group).

[Cationic Lipid (1-3)]
Cationic lipid (1) wherein
$R^{1a}$ and $R^{1b}$ are each independently an alkylene group having 1-2 carbon atoms (e.g., methylene group, ethylene group);
$X^a$ and $X^b$ are each independently $X^1$:

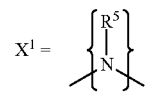

wherein $R^5$ is an alkyl group having 1-3 carbon atoms (e.g., a methyl group), or $X^2$:

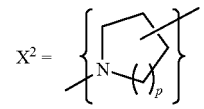

wherein p is 1 or 2;
$R^{2a}$ and $R^{2b}$ are each independently alkylene group having not more than 4 carbon atoms (e.g., methylene group, ethylene group, propylene group);
$Y^a$ and $Y^b$ are each independently an ester bond or an amide bond;
$Z^a$ and $Z^b$ are each independently $Z^1$:

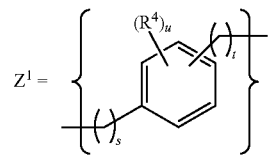

wherein s is an integer of 0-1, t is an integer of 0-2, u is an integer of 0-2 (preferably 0), and $R^4$ in the number of u are each independently a substituent; and
$R^{3a}$ and $R^{3b}$ are each independently a residue derived from a reaction product of a liposoluble vitamin having a hydroxyl group (e.g., tocopherol) and succinic anhydride, or an aliphatic hydrocarbon group having 13-17 carbon atoms (e.g., heptadecenyl group, heptadecadienyl group, 1-hexylnonyl group).

Specific examples of the cationic lipid (1) of the present invention include the following O-Ph-P3C1, O-Ph-P4O1, O-Ph-P4C2, O-Bn-P4C2, E-Ph-P4C2, L-Ph-P4C2, HD-Ph-P4C2, O-Ph-amide-P4C2, and O-Ph-C3M.

TABLE 1

| name of cationic lipid | structure |
|---|---|
| O—Ph—P3C1 | 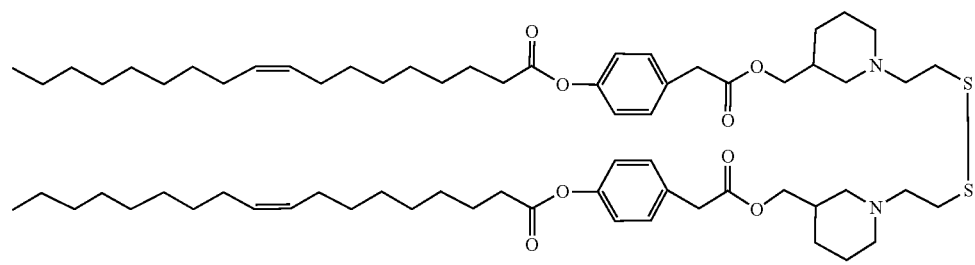 [SMILES: CCCCCCCC/C=C\CCCCCCCC(=O)Oc1ccc(CC(=O)OCC2CCCN(CCSSCCN3CCCC(COC(=O)Cc4ccc(OC(=O)CCCCCCC/C=C\CCCCCCCC)cc4)C3)C2)cc1] |

TABLE 1-continued

| name of cationic lipid | structure |
|---|---|
| O—Ph—P4C1 | 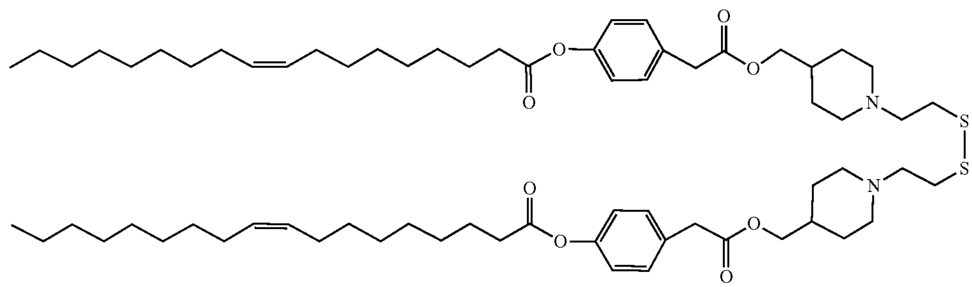 [SMILES: CCCCCCCC/C=C\CCCCCCCC(=O)Oc1ccc(CC(=O)OCC2CCN(CCSSCCN3CCC(COC(=O)Cc4ccc(OC(=O)CCCCCCC/C=C\CCCCCCCC)cc4)CC3)CC2)cc1] |
| O—Ph—P4C2 | 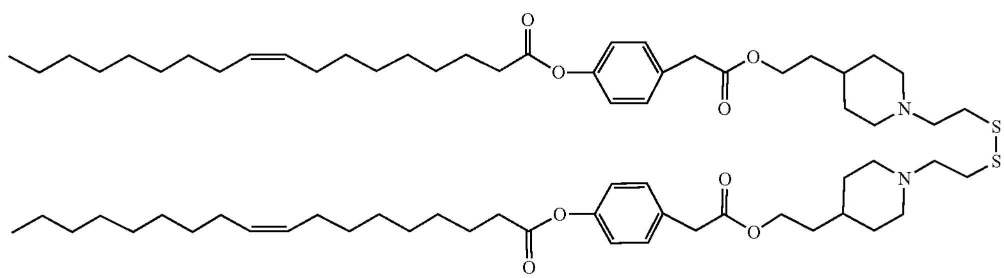 |
| O—Bn—P4C2 | 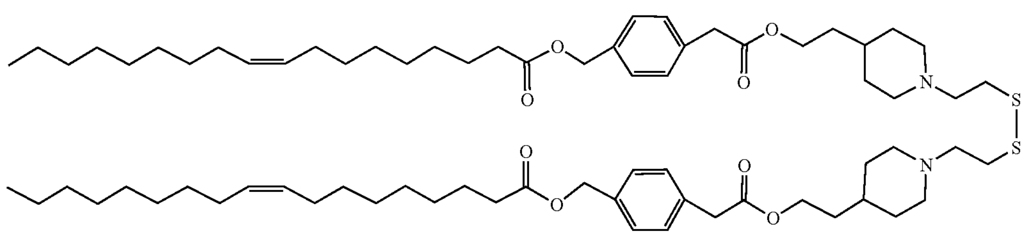 [SMILES: CCCCCCCC/C=C\CCCCCCCC(=O)OCc1ccc(CC(=O)OCCC2CCN(CCSSCCN3CCC(CCOC(=O)Cc4ccc(COC(=O)CCCCCCC/C=C\CCCCCCCC)cc4)CC3)CC2)cc1] |
| E—Ph—P4C2 | 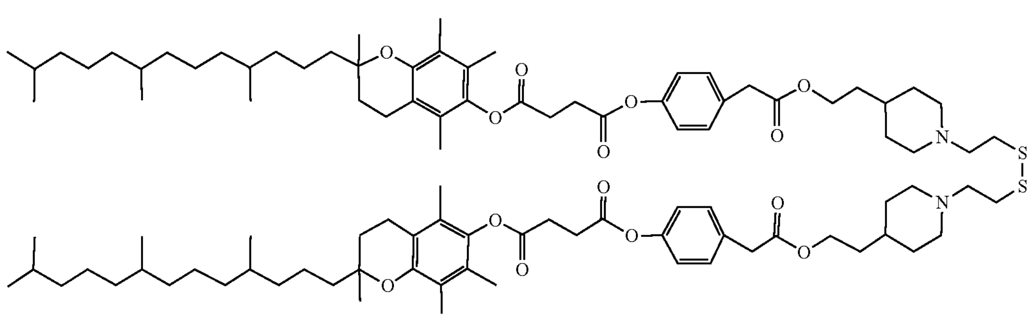 [SMILES: Cc1c(C)c2c(c(C)c1OC(=O)CCC(=O)Oc1ccc(CC(=O)OCCC3CCN(CCSSCCN4CCC(CCOC(=O)Cc5ccc(OC(=O)CCC(=O)Oc6c(C)c(C)c7c(c6C)CCC(C)(CCCC(C)CCCC(C)CCCC(C)C)O7)cc5)CC4)CC3)cc1)CCC(C)(CCCC(C)CCCC(C)CCCC(C)C)O2] |
| L—Ph—P4C2 | 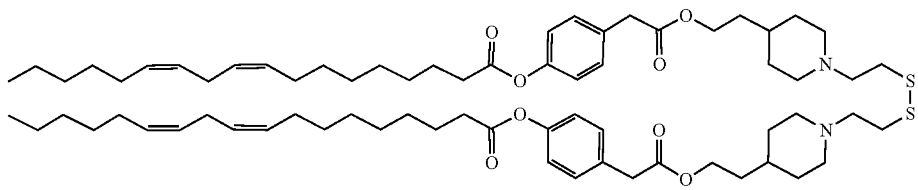 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCC/C=C\C/C=C\CCCCC)cc4)CC3)CC2)cc1] |

TABLE 1-continued

| name of cationic lipid | structure |
| --- | --- |
| HD—Ph—P4C2 | 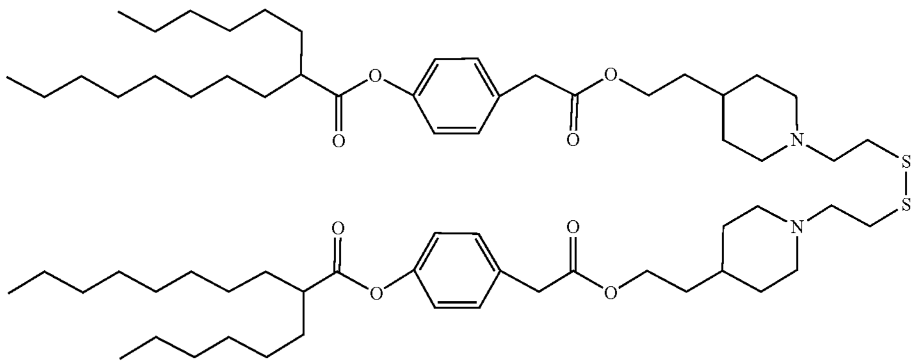 [SMILES: CCCCCCCCC(CCCCCC)C(=O)Oc1ccc(CC(=O)OCCC2CCN(CCSSCCN3CCC(CCOC(=O)Cc4ccc(OC(=O)C(CCCCCC)CCCCCCCC)cc4)CC3)CC2)cc1] |
| O—Ph-amide-P4C2 | 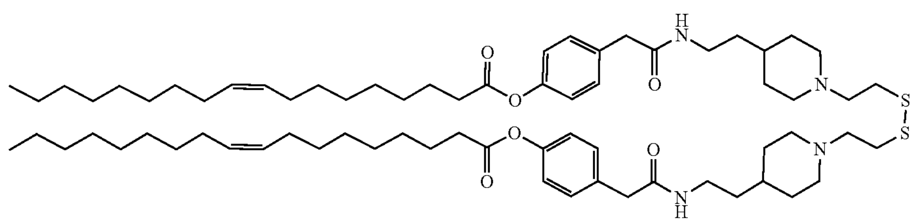 |
| O—Ph—C3M | 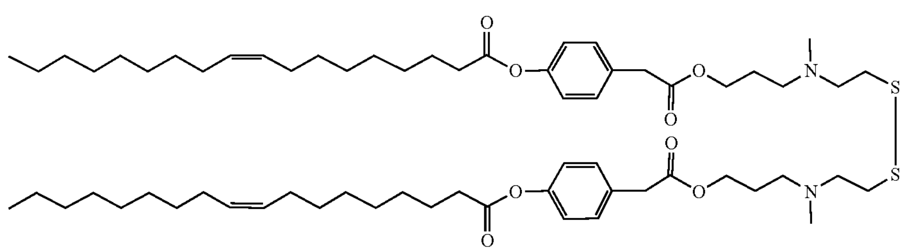 [SMILES: CCCCCCCC/C=C\CCCCCCCC(=O)Oc1ccc(CC(=O)OCCCN(C)CCSSCCN(C)CCCOC(=O)Cc2ccc(OC(=O)CCCCCCC/C=C\CCCCCCCC)cc2)cc1] |

The production method of the cationic lipid (1) of the present invention is explained now.

The cationic lipid (1) in the present invention has an —S—S— (disulfide) bond. Therefore, the production method includes, for example, a method including producing SH (thiol) compound having $R^{3a}$—CO—O—$Z^a$—$Y^a$—$R^{2a}$—$X^a$—$R^{1a}$— and SH (thiol) compound having $R^{3b}$—CO—O—$Z^b$—$Y^b$—$R^{2b}$—$X^b$—$R^{1b}$—, subjecting them to oxidation (coupling) to give the cationic lipid (1) of the present invention containing —S—S— bond, a method including sequentially bonding necessary parts to a compound containing an —S—S— bond to finally obtain the cationic lipid (1) of the present invention and the like. The latter method is preferred.

A specific example of the latter method is shown below; however, the production method is not limited thereto.

Examples of the starting compound include —S—S— bond-containing two terminal carboxylic acid, two terminal amine, two terminal isocyanate, two terminal alcohol, two terminal alcohol having a leaving group such as methanesulfonyl group and the like, a two terminal carbonate having a leaving group such as p-nitrophenylcarbonate group and the like, and the like.

For example, cationic lipid (1) wherein $R^{1a}$ and $R^{1b}$ are the same and each is $R^1$, $X^a$ and $X^b$ are the same and each is X, $R^{2a}$ and $R^{2b}$ are the same and each is $R^2$, $Y^a$ and $Y^b$ are the same and each is Y, $Z^a$ and $Z^b$ are the same and each is Z, and $R^{3a}$ and $R^{3b}$ are the same and each is $R^3$ is to be produced, a desired cationic lipid of the formula (1') can be obtained by the synthesis pathway shown below.

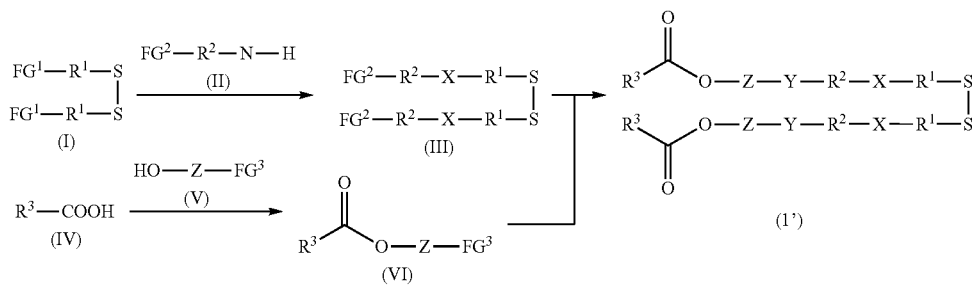

The both terminal functional groups (FG$^1$) in compound (I) containing an —S—S— bond is reacted with a secondary amine in compound (II) having the secondary amine and one functional group (FG$^2$) on the terminal to synthesize compound (III). Compound (IV) having R$^3$ is reacted with a hydroxyl group in compound (V) having the hydroxyl group and a reactive functional group (FG$^3$) to synthesize compound (VI), and finally, the reactive functional group (FG$^3$) of compound (VI) and the reactive functional group (FG$^2$) of compound (III) are reacted, whereby a cationic lipid of the formula (1') containing an —S—S— bond, R$^1$, X, R$^2$, Z and R$^3$ can be obtained.

Among the aforementioned production methods, compound (III) can be produced by the method described in patent document 2 or patent document 3.

In the reaction of compound (IV) and compound (V), a base catalyst such as potassium carbonate, sodium carbonate, potassium hydroxide, triethylamine, 4-dimethylaminopyridine (hereinafter to be referred to as "DMAP") and the like may be used as a catalyst, and the reaction may be performed in the presence of an acid catalyst such as p-toluenesulfonic acid, methanesulfonic acid and the like, or without a catalyst.

In addition, compound (IV) and compound (V) may be directly reacted using a condensing agent such as dicyclohexylcarbodiimide (hereinafter to be referred to as "DCC"), diisopropylcarbodiimide (hereinafter to be referred to as "DIC"), 1-ethyl-3-(3-dimethylaminopropyl)carbodiimide hydrochloride (hereinafter to be referred to as "EDC") and the like. Alternatively, compound (IV) may be once converted to an anhydride or the like using a condensing agent and then reacted with compound (V).

The amount of compound (IV) to be charged is generally 1-50 molar equivalents, preferably 1-10 molar equivalents, based on compound (V).

The catalyst to be used for the reaction of compound (IV) and compound (V) may be appropriately selected according to the kind of the compound to be reacted.

The amount of the catalyst is generally 0.05-100 molar equivalents, preferably 0.1-20 molar equivalents, more preferably 0.1-5 molar equivalent, relative to compound (V).

The solvent to be used for the reaction of compound (IV) and compound (V) is not particularly limited as long as it is a solvent that does not inhibit the reaction. For example, water, ethyl acetate, dichloromethane, chloroform, acetonitrile, toluene and the like can be mentioned. Among these, chloroform or toluene is preferable.

The reaction temperature is generally 0-150° C., preferably 0-80° C., more preferably 10-50° C., and the reaction time is generally 1-48 hr, preferably 1-24 hr.

The reaction product (VI) obtained by the above-mentioned reaction can be appropriately purified by a general purification method, for example, extraction purification, recrystallization, adsorption purification, reprecipitation, column chromatography, ion exchange chromatography and the like.

When compound (III) and compound (VI) are reacted, a base catalyst such as potassium carbonate, sodium carbonate, potassium hydroxide, triethylamine, 4-dimethylaminopyridine and the like may be used as a catalyst as in the reaction of compound (IV) and compound (V), and the reaction may be performed in the presence of an acid catalyst such as p-toluenesulfonic acid, methanesulfonic acid and the like, or without a catalyst.

Alternatively, compound (III) and compound (VI) may be directly reacted using a condensing agent such as DCC, DIC, EDC and the like, or compound (VI) may be treated with a condensing agent to convert the compound to an anhydride and the like, after which it may be reacted with compound (III).

The amount of compound (VI) to be charged is generally 1-50 molar equivalents, preferably 1-10 molar equivalents, relative to compound (III).

The catalyst to be used for the reaction of compound (III) and compound (VI) may be appropriately selected according to the kind of the compound to be reacted.

The amount of catalyst is generally 0.05-100 molar equivalents, preferably 0.1-20 molar equivalents, more preferably 0.1-5 molar equivalent, relative to compound (III).

The solvent to be used for the reaction of compound (III) and compound (VI) is not particularly limited as long as it is a solvent that does not inhibit the reaction. For example, water, ethyl acetate, dichloromethane, chloroform, acetonitrile, toluene and the like can be mentioned. Among these, chloroform and toluene are preferable.

The reaction temperature is generally 0 to 150° C., preferably 0 to 80° C., more preferably 10 to 50° C., and the reaction time is generally 1 hr-48 hr, preferably 2-24 hr.

The cationic lipid (1) of the present invention obtained by the above-mentioned reaction can be appropriately purified by a general purification method such as extraction purification, recrystallization, adsorption purification, reprecipitation, column chromatography, ion exchange chromatography or the like.

Specific examples are described below (see Examples 1-9). Those of ordinary skill in the art can produce a desired cationic lipid (1) by appropriately selecting the starting material and performing the reactions according to the method of the Examples in the present specification.

The lipid membrane structure of the present invention is now explained.

The lipid membrane structure of the present invention contains a cationic lipid of the present invention, i.e., a cationic lipid represented by the above-mentioned formula (1), as a membrane-constituting material. As used herein, the "lipid membrane structure" in the present invention means a particle having membrane structure wherein the hydrophilic groups of amphipathic lipid are arranged in the interface, facing the aqueous phase side. The "amphiphilic lipid" means a lipid having both a hydrophilic group showing hydrophilicity, and a hydrophobic group showing hydrophobicity. Examples of the amphiphilic lipid include cationic lipid, phospholipid and the like.

While the form of the lipid membrane structure of the present invention is not particularly limited, for example, liposome (e.g., monolayer liposome, multilayer liposome, etc.), O/W emulsion, W/O emulsion, spherical micelle, worm-like micelle, lipid nanoparticles (Lipid Nano Particle, hereinafter to be referred to as "LNP"), disordered layer structure and the like can be mentioned as a form of the cationic lipid of the present invention dispersed in an aqueous solvent. The lipid membrane structure of the present invention is preferably a liposome. In another embodiment of the present invention, the lipid membrane structure of the present invention is preferably LNP.

The lipid membrane structure of the present invention may further contain other constituent components in addition to the cationic lipid of the present invention. Examples of other constituent component include lipid (phospholipid (phosphatidylinositol, phosphatidylethanolamine, phosphatidylserine, phosphatidic acid, phosphatidylglycerol, phosphatidylcholine etc.), glycolipid, peptide lipid, cholesterol, cationic lipid other than the cationic lipid of the present invention, PEG lipid etc.), surfactant (e.g., 3-[(3-cholamidopropyl)dimethylammonio]propanesulfonate, sodium cholate salt, octylglycoside, N-D-gluco-N-methylalkanamides etc.), polyethylene glycol, protein and the like. The content of other constituent components in the lipid membrane structure of the present invention is generally 5-95 mol %, preferably 10-90 mol %, more preferably 30-80 mol %.

While the content of the cationic lipid of the present invention to be contained in the lipid membrane structure of the present invention is not particularly limited, when the lipid membrane structure is used as the below-mentioned nucleic acid-introducing agent, it is generally an amount sufficient for introducing the nucleic acid. For example, the cationic lipid of the present invention is contained in 5-100 mol %, preferably 10-90 mol %, more preferably 20-70 mol %, of the total lipid.

The lipid membrane structure of the present invention can be prepared by dispersing the cationic lipid of the present invention and other constituent components (lipid etc.) in a suitable solvent or dispersing medium, for example, aqueous solvent and alcoholic solvent, and performing an operation to induce organization as necessary.

Examples of the "operation to induce organization" include, but are not limited to, methods known per se such as an ethanol dilution method using a micro flow path or vortex, a simple hydration method, sonication, heating, vortex, an ether injecting method, a French press method, a cholic acid method, a $Ca^{2+}$ fusion method, a freeze-thaw method, a reversed-phase evaporation method and the like.

A nucleic acid can be introduced into a cell in vivo and/or in vitro by encapsulating the nucleic acid in the lipid membrane structure containing the cationic lipid of the present invention and contacting the lipid membrane structure with the cell. Therefore, the present invention provides a nucleic acid-introducing agent, containing the above-mentioned cationic lipid or lipid membrane structure of the present invention.

The nucleic acid-introducing agent of the present invention can introduce any nucleic acid into a cell. Examples of the kind of nucleic acid include, but are not limited to, DNA, RNA, chimera nucleic acid of RNA, DNA/RNA hybrid and the like. While any nucleic acid having 1 to 3 chains can be used, it is preferably a single strand or double strand. The nucleic acid may be other type of nucleotide such as N-glycoside of purine or pyrimidine base or other oligomer having a non-nucleotide backbone (e.g., commercially available peptide nucleic acid (PNA) etc.), other oligomer containing a special bond (said oligomer comprising base pairing or a nucleotide having a configuration permitting attachment of base, which are found in DNA and RNA) and the like. Furthermore, it may be a nucleic acid added with known modification, for example, a nucleic acid with a label known in the field, a nucleic acid with a cap, a methylated nucleic acid, one or more natural nucleotides substituted by an analog, a nucleic acid with intramolecular nucleotidyl modification, for example, a nucleic acid with non-charge bond (e.g., methylphosphonate, phosphotriester, phosphoramidate, carbamate and the like), a nucleic acid with a charged bond or sulfur-containing bond (e.g., phosphorothioate, phosphorodithioate and the like), for example, a nucleic acid with a side chain group such as protein (nuclease, nuclease inhibitor, toxin, antibody, signal peptide, poly-L-lysine and the like), sugar (e.g., monosaccharide and the like) and the like, a nucleic acid with an intercalating compound (e.g., acridine, psoralen and the like), a nucleic acid with a chelate compound (e.g., metal, radioactive metal, boron, oxidative metal and the like), a nucleic acid containing an alkylating agent, or a nucleic acid with a modified bond (e.g., a anomer-type nucleic acid and the like).

The type of the DNA that can be used in the present invention is not particularly limited, and can be selected as appropriate according to the purpose of use. For example, plasmid DNA, cDNA, antisense DNA, chromosomal DNA, PAC, BAC, CpG oligosaccharide, and the like can be mentioned. Preferred are plasmid DNA, cDNA and antisense DNA, and more preferred is plasmid DNA. A circular DNA such as plasmid DNA and the like can be digested as appropriate with a restriction enzyme and the like, and also used as a linear DNA.

The type of the RNA that can be used in the present invention is not particularly limited, and can be selected as appropriate according to the purpose of use. For example, siRNA, miRNA, shRNA, antisense RNA, messenger RNA (mRNA), single strand RNA genome, double strand RNA genome, RNA replicon, transfer RNA, ribosomal RNA and the like can be mentioned, with preference given to siRNA, miRNA, shRNA, mRNA, antisense RNA, and RNA replicon.

The nucleic acid used in the present invention is preferably purified by a method generally used by those of ordinary skill in the art.

The nucleic acid-introducing agent of the present invention encapsulating a nucleic acid can be administered in vivo for the purpose of, for example, prevention and/or treatment of diseases. Therefore, the nucleic acid to be used in the present invention is preferably one having a preventive and/or therapeutic activity against a given disease (prophylactic/therapeutic nucleic acid). Examples of such nucleic acid include nucleic acids and the like used for so-called gene therapy.

To introduce a nucleic acid into cells by the use of the nucleic acid-introducing agent of the present invention, the lipid membrane structure of the present invention encapsulating the nucleic acid is formed by the co-presence of the object nucleic acid when forming the lipid membrane structure of the present invention. For example, when a liposome is formed by an ethanol dilution method, an aqueous nucleic acid solution and a solution of the constituent components (lipid etc.) of the lipid membrane structure of the present invention in an ethanol are vigorously mixed in a vortex, micro flow path and the like, and the mixture is diluted with an appropriate buffer. When a liposome is formed by a simple hydration method, the constituent components (lipid etc.) of the lipid membrane structure of the present invention are dissolved in an appropriate organic solvent, and the solution is placed in a glass container and dried under reduced pressure to evaporate the solvent, whereby a lipid thin film is obtained. Thereto is added an aqueous nucleic acid solution and, after hydration, the mixture is sonicated by a sonicator. The present invention also provides such above-mentioned lipid membrane structure encapsulating a nucleic acid.

One form of the lipid membrane structure encapsulating a nucleic acid is, for example, LNP encapsulating a nucleic acid by forming an electrostatic complex between the nucleic acid and a cationic lipid. This LNP can be used as a drug delivery system for selectively delivering a nucleic acid and the like into a particular cell, and is useful for, for example, DNA vaccines, gene therapy drugs for tumor, nucleic acid pharmaceutical products that suppress expression of target genes by utilizing RNA interference, and the like, by introducing antigen gene into dendritic cells.

The particle size of the lipid membrane structure of the present invention encapsulating a nucleic acid is not particularly limited, and is preferably 10 nm-500 nm, more preferably 30 nm-300 nm. The particle size can be measured by using a particle size distribution measuring device such as Zetasizer Nano (Malvern) or the like. The particle size of the lipid membrane structure can be appropriately adjusted by the method for preparing the lipid membrane structure.

The surface charge (zeta potential) of the lipid membrane structure of the present invention encapsulating the nucleic acid is not particularly limited and preferably −15 to +15 mV, more preferably −10 to +10 mV. In conventional transgene, particles electrically charged to have a plus surface potential have been mainly used. This is useful as a method for promoting electrostatic interactions with heparin sulfate on the negatively-charged cell surface to enhance uptake into cells. However, the positive surface charge may suppress, in the cell, release of nucleic acid from the carrier due to the interaction with a nucleic acid to be delivered or protein synthesis due to the interaction between mRNA and a nucleic acid to be delivered. This problem can be solved by adjusting the surface charge to fall within the above-mentioned range. The surface charge can be measured using a zeta potential measuring apparatus such as Zetasizer Nano and the like. The surface charge of the lipid membrane structure can be adjusted by the composition of the constituent component of the lipid membrane structure containing the cationic lipid of the present invention.

The lipid membrane surface pKa (hereinafter to be referred to as Liposomal pKa) of the lipid membrane structure of the present invention is not particularly limited, and pKa is preferably 5.5-7.2, further preferably 6.0-6.8. Liposomal pKa is used as an index indicating the susceptibility of the lipid membrane structure which is incorporated by endocytosis to protonation in the endosome in a weakly acidic environment inside the endosome. As described in non-patent documents 3 and 4, to escape from the endosome and deliver the nucleic acid into the left atrium, it is important to set the Liposomal pKa to a value preferable for the escape from the endosome. By adjusting the Liposomal pKa to fall within the above ranges, the nucleic acid can be efficiently delivered into the cytoplasm. The Liposomal pKa can be adjusted by the composition of the constituent components of the lipid membrane structure containing the cationic lipid of the present invention.

The hemolysis activity (membrane fusion capacity) of the lipid membrane structure of the present invention is not particularly limited. Preferably, the lipid membrane structure does not show hemolysis activity (less than 5%) at physiological pH (pH 7.4), but shows the activity under an endosomal weakly acidic environment (pH 5.5). As described in non-patent document 5, hemolysis is one of the means by which the lipid membrane structure incorporated by endocytosis escapes from the endosome. Higher hemolysis activity enables efficient delivery of the nucleic acid into the cytoplasm. However, when hemolysis activity is present at physiological pH, the nucleic acid is also delivered to unintended cells during retention in blood, which in turn leads to decreased targeting and toxicity. Therefore, it is preferable to have hemolysis activity only in the endosome environment as described above. The hemolysis activity can be adjusted by the composition of the constituent components of the lipid membrane structure containing a cationic lipid of the present invention.

The lipid membrane structure of the present invention encapsulating the nucleic acid is brought into contact with cells to introduce the encapsulated nucleic acid into the cells. The kind of the cell is not particularly limited, a prokaryotic or eukaryotic cell can be used, with preference given to eukaryote. The kind of the eukaryote is not particularly limited and, for example, vertebrates such as mammals including human (e.g., human, monkey, mouse, rat, hamster, bovine etc.), birds (e.g., chicken, ostrich etc.), *amphibia* (e.g., frog etc.), fishes (e.g., zebrafish, rice-fish etc.) and the like, invertebrates such as insects (silk moth, moth, *Drosophila* etc.) and the like, plants, microorganisms (e.g., yeasts), and the like can be mentioned. More preferably, the target cell in the present invention is an animal or plant cell, more preferably a mammalian cell. The cell may be a culture cell line including a cancer cell, or a cell isolated from an individual or tissue, or a cell of a tissue or tissue piece. The cell may be an adherent cell or a non-adherent cell.

The step of contacting the lipid membrane structure of the present invention encapsulating the nucleic acid with the cell in vitro is specifically explained below.

The cells are suspended in a suitable medium several days before contact with the lipid membrane structure, and cultured under appropriate conditions. At the time of contact with the lipid membrane structure, the cells may or may not be in a proliferative phase.

The culture medium on contact may be a serum-containing medium or a serum-free medium, wherein the serum concentration of the medium is preferably not more than 30 wt %, more preferably not more than 20 wt %, since when the medium contains excess protein such as serum and the like, the contact between the lipid membrane structure and the cell may be inhibited.

The cell density on contact is not particularly limited, and can be appropriately determined in consideration of the kind of the cell and the like. It is generally within the range of $1 \times 10^4$-$1 \times 10^7$ cells/mL.

A suspension of the aforementioned lipid membrane structure of the present invention enclosing the nucleic acid is added to the thus-prepared cells. The amount of the suspension to be added is not particularly limited, and can be appropriately determined in consideration of the cell number and the like. The concentration of the lipid membrane structure to be contacted with the cells is not particularly limited as long as the desired introduction of the nucleic acid into the cells can be achieved. The lipid concentration is generally 1-100 nmol/ml, preferably 10-50 nmol/ml, and the concentration of the nucleic acid is generally 0.01-100 µg/ml, preferably 0.1-10 µg/ml.

After the aforementioned suspension is added to cells, the cells are cultured. The temperature, humidity and $CO_2$ concentration during culturing are appropriately determined in consideration of the kind of the cell. When the cell is derived from a mammal, generally, the temperature is about 37° C., humidity is about 95% and $CO_2$ concentration is about 5%. While the culture period can also be appropriately determined in consideration of the conditions such as the kind of the cell and the like, it is generally a range of 0.1-76 hr, preferably a range of 0.2-24 hr, more preferably a range of 0.5-12 hr. When the above-mentioned culture time is too short, the nucleic acid is not sufficiently introduced into the cells, and when the culture time is too long, the cells may become weak.

By the above-mentioned culture, the nucleic acid is introduced into cells. The culture is further continued preferably by exchanging the medium with a fresh medium, or adding a fresh medium to the medium. When the cell is a mammal-derived cell, the fresh medium preferably contains a serum or nutrition factor.

As mentioned above, a nucleic acid can be introduced into cells not only outside the body (in vitro) but also in the body (in vivo) by using the lipid membrane structure of the present invention. That is, by administration of the lipid membrane structure of the present invention encapsulating the nucleic acid to a subject, the lipid membrane structure reaches and contacts with the target cells, and the nucleic acid encapsulated in the lipid membrane structure is introduced into the cells in vivo. The subject to which the lipid membrane structure can be administered is not particularly limited and, for example, vertebrates such as mammals (e.g., human, monkey, mouse, rat, hamster, bovine etc.), birds (e.g., chicken, ostrich etc.), *amphibia* (e.g., frog etc.), fishes (e.g., zebrafish, rice-fish etc.) and the like, invertebrates such as insects (e.g., silk moth, moth, *Drosophila* etc.) and the like, plants and the like can be mentioned. The subject of administration of the lipid membrane structure of the present invention is preferably human or other mammal.

The kind of the target cell is not particularly limited, and a nucleic acid can be introduced into cells in various tissues (e.g., liver, kidney, pancreas, lung, spleen, heart, blood, muscle, bone, brain, stomach, small intestine, large intestine, skin, adipose tissue, lymph node, tumor, etc.) by using the lipid membrane structure of the present invention.

The administration method of the lipid membrane structure into which a nucleic acid and/or a compound other than nucleic acid is introduced to a target (e.g., vertebrate, invertebrate and the like) is not particularly limited as long as the lipid membrane structure reaches and contacts with the target cells, and the compound introduced into the lipid membrane structure can be introduced into the cell, and an administration method known per se (e.g., oral administration, parenteral administration (e.g., intravenous administration, intramuscular administration, topical administration, transdermal administration, subcutaneous administration, intraperitoneal administration, spray etc.) etc.) can be appropriately selected in consideration of the kind of the compound to be introduced, the kind and the site of the target cell and the like. The dose of the lipid membrane structure is not particularly limited as long as the introduction of the compound into the cells can be achieved, and can be appropriately selected in consideration of the kind of the subject of administration, administration method, the kind of the compound to be introduced, the kind and the site of the target cell and the like.

When the cationic lipid or lipid membrane structure of the present invention is used as a nucleic acid-introducing agent, they can be formulated according to a conventional method.

When the nucleic acid-introducing agent is provided as a reagent for studies, the lipid membrane structure of the present invention may be provided as it is as the nucleic acid-introducing agent of the present invention, or the nucleic acid-introducing agent of the present invention may be provided as a sterile solution or suspension with, for example, water or other physiologically acceptable liquid (e.g., water-soluble solvent (e.g., malic acid buffer etc.), organic solvent (e.g., ethanol, methanol, DMSO, tert-butanol and the like), or a mixture of aqueous solvent and organic solvent etc.). The nucleic acid-introducing agent of the present invention may appropriately contain physiologically acceptable additive (e.g., excipient, vehicle, preservative, stabilizer, binder etc.), which are known per se.

When the nucleic acid-introducing agent is provide as a medicament, the lipid membrane structure of the present invention may be used as it is as the nucleic acid-introducing m agent of the present invention or the nucleic acid-introducing agent of the present invention may be produced as an oral preparation (for example, tablet, capsule etc.) or a parenteral agent (for example, injection, spray etc.), preferably a parenteral agent (more preferably, injection) by blending with a pharmaceutically acceptable known additives such as carrier, flavor, excipient, vehicle, preservative, stabilizer, binder and the like in a conventionally-admitted unit dosage form required for practicing preparation formulation.

The nucleic acid-introducing agent of the present invention can be formulated into a preparation not only for adults but also for children.

The nucleic acid-introducing agent of the present invention can also be provided in the form of a kit. The kit can contain, in addition to the cationic lipid or lipid membrane structure of the present invention, a reagent used for the introduction of a nucleic acid. In one embodiment, the nucleic acid-introducing agent (or kit) of the present invention further contains a polycation (e.g., protamine). Using the nucleic acid-introducing agent (or kit) of the present invention in this embodiment, an electrostatic complex of nucleic acid and polycation (e.g., protamine) can be encapsulated in the lipid membrane structure of the present invention, whereby the nucleic acid can be subjected to the intracellular introduction.

EXAMPLE

The Examples of the present invention are explained in further detail in the following, but the present invention is not limited in any way by the Examples.

The abbreviations used in the explanation of Examples each mean the following.
 siRNA: small interfering RNA
 mRNA: messenger RNA
 Chol: cholesterol
 DMG-PEG2k: 1,2-dimyristoyl-sn-glycerol, methoxypolyethylene glycol (PEG MW 2000)
 DSG-PEG5k: 1,2-distearoyl-sn-glycerol, methoxypolyethylene glycol (PEG MW 5000)
 DOPE: 1,2-dioleoyl-sn-glycero-3-phosphoethanolamine DOPC: 1,2-dioleoyl-sn-glycero-3-phosphocholine
PBS: phosphate buffered saline
MES: 2-morpholinoethanesulfonic acid
TNS: sodium 6-(p-toluidino)-2-naphthalenesulfonate Table 1 shows the names and structures of the cationic lipids produced in the following Examples and Comparative Examples. In Comparative Examples 1 and 2, the production followed the production method of patent document 2.

TABLE 2

| | name of cationic lipid | structure |
|---|---|---|
| Example 1 | O—Ph—P3C1 | 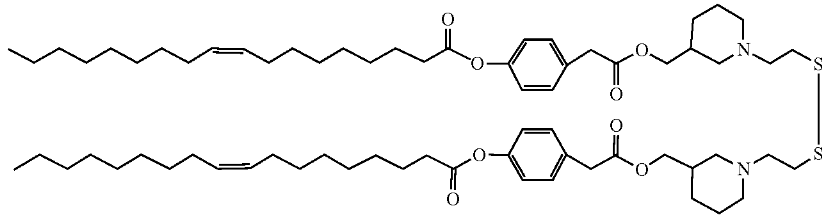 [SMILES: CCCCCCCC/C=C\CCCCCCCC(=O)COc1ccc(CC(=O)OCC2CCCN(CCSSCCN3CCCC(COC(=O)Cc4ccc(OC(=O)CCCCCCC/C=C\CCCCCCCC)cc4)C3)C2)cc1] |
| Example 2 | O—Ph—P4C1 | 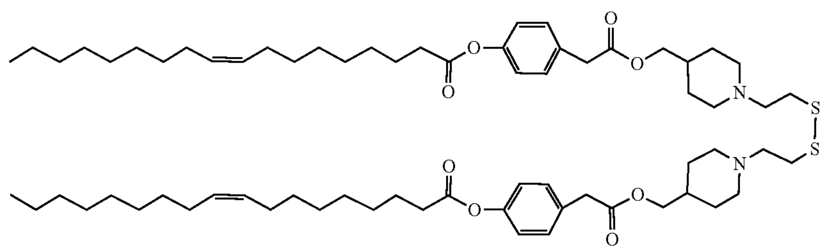 [SMILES: CCCCCCCC/C=C\CCCCCCCC(=O)Oc1ccc(CC(=O)OCC2CCN(CCSSCCN3CCC(COC(=O)Cc4ccc(OC(=O)CCCCCCC/C=C\CCCCCCCC)cc4)CC3)CC2)cc1] |
| Example 3 | O—Ph—P4C2 | 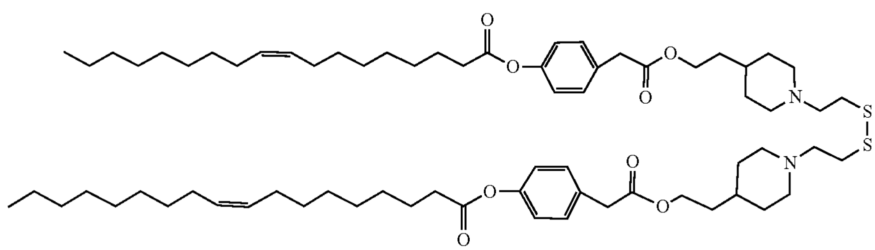 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1] |
| Example 4 | O—Bn—P4C2 | 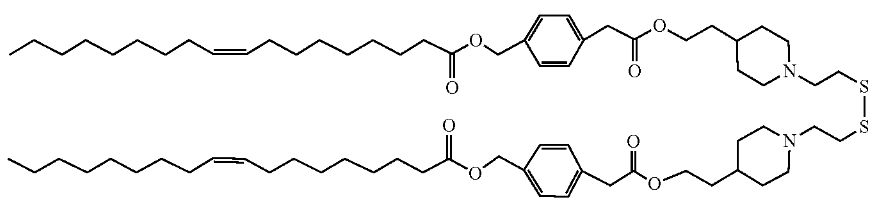 [SMILES: CCCCCCCC/C=C\CCCCCCCC(=O)OCc1ccc(CC(=O)OCCC2CCN(CCSSCCN3CCC(CCOC(=O)Cc4ccc(COC(=O)CCCCCCC/C=C\CCCCCCCC)cc4)CC3)CC2)cc1] |
| Example 5 | E—Ph—P4C2 | 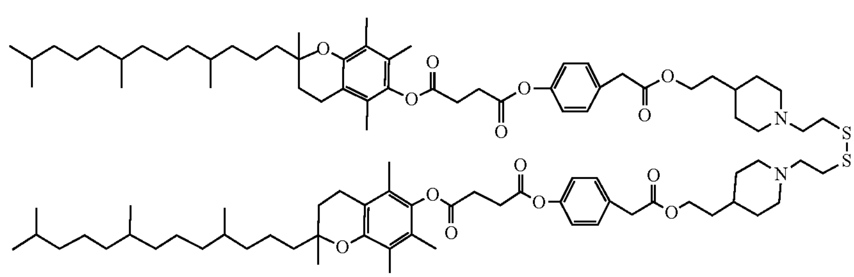 [SMILES: Cc1c(C)c2c(c(C)c1OC(=O)CCC(=O)Oc1ccc(CC(=O)OCCC3CCN(CCSSCCN4CCC(CCOC(=O)Cc5ccc(OC(=O)CCC(=O)Oc6c(C)c(C)c7c(c6C)CCC(C)(CCCC(C)CCCC(C)CCCC(C)C)O7)cc5)CC4)CC3)cc1)CCC(C)(CCCC(C)CCCC(C)CCCC(C)C)CO2] |
| Example 6 | L—Ph—P4C2 | 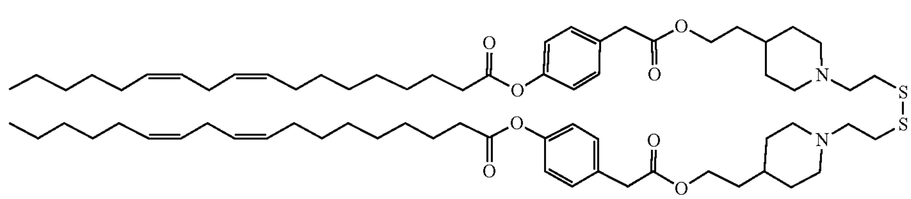 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCC/C=C\C/C=C\CCCCC)cc4)CC3)CC2)cc1] |

TABLE 2-continued
| | name of cationic lipid | structure |
|---|---|---|
| Example 7 | HD—Ph—P4C2 | 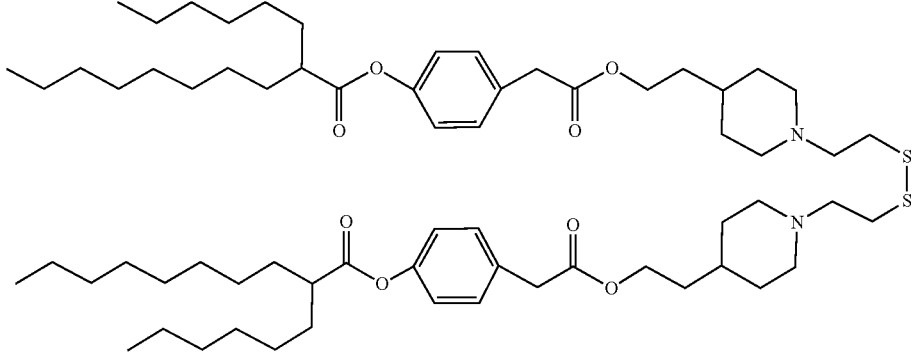 [SMILES: CCCCCCCCC(CCCCCC)C(=O)Oc1ccc(CC(=O)OCCC2CCN(CCSSCCN3CCC(CCOC(=O)Cc4ccc(OC(=O)C(CCCCCC)CCCCCCCC)cc4)CC3)CC2)cc1] |
| Example 8 | O—Ph-amide-P4C2 | 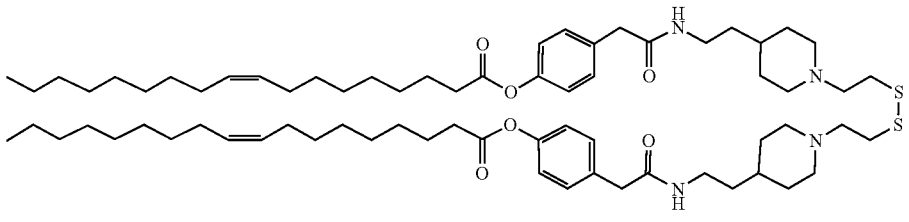 |
| Example 9 | O—Ph—C3M | 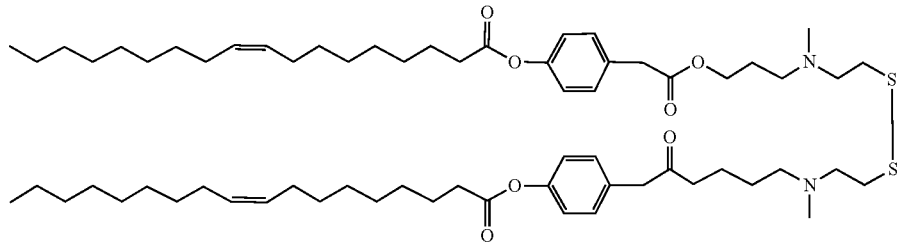 [SMILES: CCCCCCCC/C=C\CCCCCCCC(=O)Oc1ccc(CC(=O)CCCCN(C)CCSSCCN(C)CCCOC(=O)Cc2ccc(OC(=O)CCCCCCC/C=C\CCCCCCCC)cc2)cc1] |
| Comparative Example 1 | O—P4C2 | 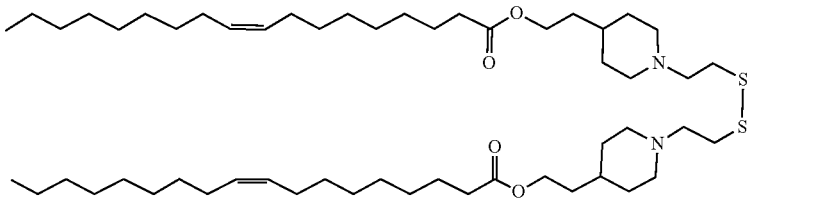 [SMILES: CCCCCCCC/C=C\CCCCCCCC(=O)OCCC1CCN(CCSSCCN2CCC(CCOC(=O)CCCCCCC/C=C\CCCCCCCC)CC2)CC1] |
| Comparative Example 2 | E—P4C2 | 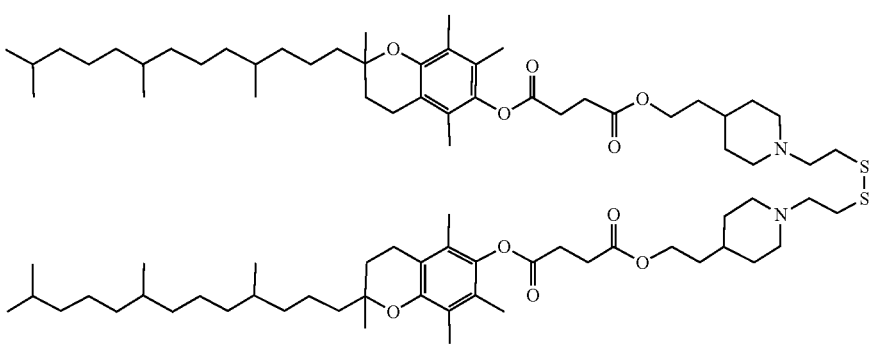 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

[Example 1] Synthesis of O-Ph-P3C1

While O-Ph-P3C1 was produced by the method of the formula (2), the production thereof is not limited to this method.

The formula (2)

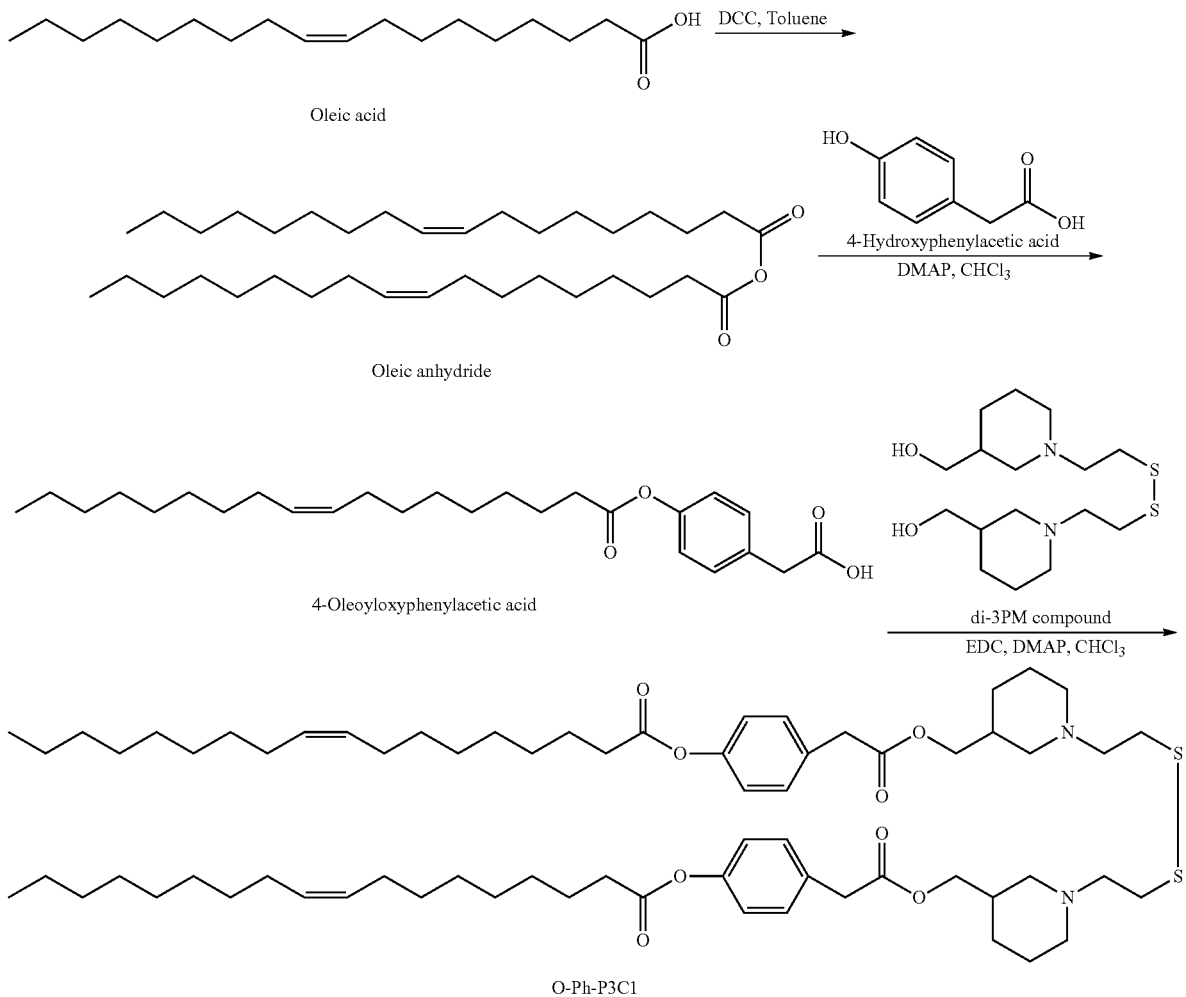

<Acid Anhydridation of Oleic Acid>

Oleic acid (manufactured by NOF CORPORATION) (70.0 g, 248 mmol) was dissolved in chloroform (560 g) at room temperature, and the mixture was cooled to 10-15° C. Thereto was added dropwise a suspension of DCC (manufactured by Osaka Synthetic Chemical Laboratories, Inc.) (25.1 g, 121 mmol) dissolved in chloroform (140 g), and the mixture was reacted at 10-25° C. for 2 hr. The reaction solution was filtered, and the filtrate was concentrated by an evaporator. The obtained concentrate was re-dissolved in hexane (210 g), and insoluble material was removed by filtration. The obtained filtrate was concentrated by an evaporator to give oleic anhydride (64.2 g).

$^1$H-NMR spectrum (600 MHz, CDCl$_3$) of oleic anhydride

δ0.86-0.90 ppm (t, 6H), δ1.25-1.40 ppm (m, 40H), δ1.61-1.68 (m, 4H), δ1.94-2.05 (m, 8H), δ2.39-2.46 (t, 4H), δ5.30-5.38 (m, 4H)

<Synthesis of 4-oleoyloxyphenylacetic Acid>

Oleic anhydride (43.1 g, 78.9 mmol) and 4-hydroxyphenylacetic acid (manufactured by Tokyo Chemical Industry Co., Ltd.) (6.00 g, 39.4 mmol) were dissolved in chloroform (647 g). Thereto was added DMAP (manufactured by KOEI CHEMICAL CO., LTD.) (1.93 g, 15.8 mmol) and the mixture was reacted at room temperature for 9 hr. The reaction solution was washed twice with 10% aqueous acetic acid solution (216 g) and twice with ion exchange water (216 g). Magnesium sulfate (manufactured by KANTO CHEMICAL CO., INC.) (12.9 g) was added to the organic layer, and the mixture was stirred for 30 min. Magnesium sulfate was filtered off, and the filtrate was concentrated by an evaporator. The concentrate was re-dissolved in hexane (284 g), the insoluble material was filtered off, and the filtrate was extracted 6 times with acetonitrile (168 g). The acetonitrile layer was recovered and concentrated by an evaporator to give a crude product (18.1 g). The obtained crude product (14.5 g) was subjected to column purification to give 4-oleoyloxyphenylacetic acid (3.66 g).

$^1$H-NMR spectrum (600 MHz, CDCl$_3$) of 4-oleoyloxyphenylacetic acid

δ0.77-0.89 (t, 3H), δ1.27-1.42 (m, 20H), δ1.71-1.77 (m, 2H), δ1.99-2.03 (m, 4H), δ2.52-2.56 (m, 2H), δ3.64 (s, 2H), δ5.32-5.38 (m, 2H), δ7.03-7.06 (m, 2H), δ7.28-7.31 (m, 2H)

<Synthesis of O-Ph-P3C1>

Bis{2-[3-(hydroxymethyl)piperidyl]ethyl}disulfide (di-3PM form) 0.340 g, 0.975 mmol) synthesized by the method described in patent document 2,4-oleoyloxyphenylacetic acid (0.813 g, 1.95 mmol), and DMAP (0.0477 g, 0.390 mmol) were dissolved in chloroform (10.2 g) at room temperature. Thereto was added EDC (manufactured by Tokyo Chemical Industry Co., Ltd.) (0.561 g, 2.93 mmol), and the mixture was reacted at 30-35° C. for 3 hr. The reaction solution was washed twice with 20% brine (6.80 g) and dehydrated using magnesium sulfate (0.340 g). Magnesium sulfate was filtered off, and the filtrate was concentrated in an evaporator to give a crude product (0.870 g). The obtained crude product was subjected to column purification to give O-Ph-P3C1 (0.584 g).

$^1$H-NMR spectrum (600 MHz, CDCl$_3$) of O-Ph-P3O1

δ0.86-0.90 (t, 6H), δ0.92-1.05 (m, 2H), δ1.20-1.42 (m, 40H), δ1.50-1.60 (m, 2H), δ1.62-1.80 (m, 10H), δ1.90-2.04 (m, 12H), δ2.52-2.56 (m, 4H), δ2.61-2.65 (m, 4H), δ2.78-2.82 (m, 8H), δ3.61 (s, 4H), δ3.89-4.02 (m, 4H), δ5.34-5.37 (m, 4H), δ7.02-7.05 (m, 4H), δ7.26-7.30 (m, 4H)

[Example 2] Synthesis of O-Ph-P4C1

O-Ph-P4C1 was synthesized by the same synthetic pathway as in Example 1.

Bis{2-[4-(hydroxymethyl)piperidyl]ethyl}disulfide (di-4PM form) 0.340 g, 0.975 mmol) synthesized by the method described in patent document 2,4-oleoyloxyphenylacetic acid (0.853 g, 2.05 mmol), and DMAP (0.0477 g, 0.390 mmol) were dissolved in chloroform (10.2 g) at room temperature. Thereto was added EDC (0.561 g, 2.93 mmol), and the mixture was reacted at 30-35° C. for 3 hr. The reaction solution was washed twice with 20% brine (6.80 g) and dehydrated using magnesium sulfate (0.340 g). Magnesium sulfate was filtered off, and the filtrate was concentrated in an evaporator to give a crude product (0.900 g). The obtained crude product was subjected to column purification to give O-Ph-P4C1 (0.629 g).

$^1$H-NMR spectrum (600 MHz, CDCl$_3$) of O-Ph-P4C1

δ0.86-0.90 (t, 6H), δ1.27-1.42 (m, 44H), δ1.62-1.76 (m, 10H), δ1.96-2.00 (m, 12H), δ2.52-2.56 (m, 4H), δ2.64-2.67 (m, 4H), δ2.81-2.93 (m, 8H), δ3.60 (s, 4H), δ3.93-3.95 (d, 4H), δ5.34-5.37 (m, 4H), δ7.02-7.05 (m, 4H), δ7.26-7.30 (m, 4H)

[Example 3] Synthesis of O-Ph-P4C2

O-Ph-P4C2 was synthesized by the same synthetic pathway as in Example 1.

Bis{2-[4-(2-hydroxyethyl)piperidyl]ethyl}disulfide (di-4PE form) (0.350 g, 0.929 mmol) synthesized by the method described in patent document 2,4-oleoyloxyphenylacetic acid (0.813 g, 1.95 mmol), and DMAP (0.0454 g, 0.372 mmol) were dissolved in chloroform (10.5 g) at room temperature. Thereto was added EDC (0.534 g, 2.79 mmol), and the mixture was reacted at 30-35° C. for 4 hr. The reaction solution was washed twice with 20% brine (7.00 g) and dehydrated using magnesium sulfate (0.350 g). Magnesium sulfate was filtered off, and the filtrate was concentrated in an evaporator to give a crude product (1.10 g). The obtained crude product was subjected to column purification to give O-Ph-P4C2 (0.722 g).

$^1$H-NMR spectrum (600 MHz, CDCl$_3$) of O-Ph-P4C2

δ0.86-0.90 (t, 6H), δ1.22-1.42 (m, 46H), δ1.54-1.76 (m, 12H), δ1.94-2.03 (m, 12H), δ2.52-2.56 (m, 4H), δ2.62-2.66 (m, 4H), δ2.80-2.89 (m, 8H), δ3.59 (s, 4H), δ4.11-4.14 (t, 4H), δ5.34-5.37 (m, 4H), δ7.02-7.05 (m, 4H), δ7.26-7.30 (m, 4H)

[Example 4] O-Bn-P4C2

O-Bn-P4C2 was synthesized by the same synthetic pathway as in Example 1.

<Synthesis of 4-(oleoyloxymethyl)phenylacetic Acid>

Oleic anhydride (13.2 g, 24.1 mmol) and 4-(hydroxymethyl)phenylacetic acid (manufactured by Tokyo Chemical Industry Co., Ltd.) (2.01 g, 12.1 mmol) were dissolved in chloroform (198 g). Thereto was added DMAP (0.590 g, 4.83 mmol) and the mixture was reacted at room temperature for 7 hr. The reaction solution was washed twice with 10% aqueous acetic acid solution (66 g) and twice with ion exchange water (66 g). Magnesium sulfate (manufactured by KANTO CHEMICAL CO., INC.) (4.00 g) was added to the organic layer, and the mixture was stirred for 30 min. Magnesium sulfate was filtered off, and the filtrate was concentrated by an evaporator. The concentrate was re-dissolved in hexane (87.0 g), the insoluble material was filtered off, and the filtrate was extracted 6 times with acetonitrile (51.5 g). The acetonitrile layer was recovered and concentrated by an evaporator to give a crude product (7.47 g). The obtained crude product (5.985 g) was subjected to column purification to give 4-(oleoyloxymethyl)phenylacetic acid (1.03 g).

$^1$H-NMR spectrum (600 MHz, CDCl$_3$) of 4-(oleoyloxymethyl)phenylacetic acid

δ0.86-0.89 (t, 3H), δ1.15-1.37 (m, 20H), δ1.60-1.66 (m, 2H), δ1.98-2.04 (m, 4H), δ2.32-2.36 (m, 2H), δ3.66 (s, 2H), δ5.09 (s, 2H), δ5.31-5.38 (m, 2H), δ7.25-7.29 (m, 2H), δ7.31-7.44 (m, 2H)

<Synthesis of O-Bn-P4C2>

Di-4PE form (0.250 g, 0.664 mmol), 4-(oleoyloxymethyl)phenylacetic acid (0.600 g, 1.39 mmol), and DMAP (0.0324 g, 0.266 mmol) were dissolved in chloroform (7.5 g) at room temperature. Thereto was added EDC (0.382 g, 1.99 mmol), and the mixture was reacted at 30-35° C. for 4 hr. The reaction solution was washed twice with 20% brine (5.00 g) and dehydrated using magnesium sulfate (0.250 g). Magnesium sulfate was filtered off, and the filtrate was concentrated in an evaporator to give a crude product (0.823 g). The obtained crude product was subjected to column purification to give O-Bn-P4C2 (0.463 g).

$^1$H-NMR spectrum (600 MHz, CDCl$_3$) of O-Bn-P4C2

δ0.86-0.89 (t, 6H), δ1.20-1.30 (m, 46H), δ1.50-1.65 (m, 12H), δ1.92-2.03 (m, 12H), δ2.32-2.36 (t, 4H), δ2.62-2.65 (m, 4H), δ2.80-2.90 (m, 8H), δ3.61 (s, 4H), δ4.11-4.14 (t, 4H), δ5.09 (s, 4H), δ5.31-5.38 (m, 4H), δ7.26-7.28 (m, 4H), δ7.30-7.32 (m, 4H)

[Example 5] E-Ph-P4C2

E-Ph-P4C2 was synthesized by the same synthetic pathway as in Example 1.

<Acid Anhydridation of Succinic Acid D-α-Tocopherol>

Succinic acid D-α-tocopherol (manufactured by SIGMA-ALDRICH) (70.0 g, 132 mmol) was dissolved in chloroform (560 g) at room temperature, and the mixture was cooled to 10-15° C. Thereto was added dropwise a suspension of DCC (manufactured by Osaka Synthetic Chemical Laboratories, Inc.) (13.7 g, 66 mmol) dissolved in chloroform (140 g), and the mixture was reacted at 10-25° C. for 2 hr. The reaction solution was filtered, and the filtrate was concentrated by an evaporator. The obtained concentrate was re-dissolved in hexane (210 g), and insoluble material was removed by filtration. The obtained filtrate was concentrated by an evaporator to give succinic anhydride D-α-tocopherol (64.2 g).

¹H-NMR spectrum (600 MHz, CDCl₃) of succinic anhydride D-α-tocopherol

δ0.84-0.87 ppm (m, 24H), δ1.02-1.85 ppm (m, 52H), δ1.96 (s, 6H), δ2.01 (s, 6H), δ2.08 (s, 6H), δ2.56-2.59 (t, 4H), δ2.90-2.95 (m, 8H)

<Synthesis of 4-(D-α-tocopherol hemisuccinyl)phenylacetic Acid>

Succinic anhydride D-α-tocopherol (43.1 g, 41.3 mmol) and 4-hydroxyphenylacetic acid (manufactured by Tokyo Chemical Industry Co., Ltd.) (3.13 g, 20.6 mmol) were dissolved in chloroform (647 g). Thereto was added DMAP (manufactured by KOEI CHEMICAL CO., LTD.) (1.01 g, 8.26 mmol) and the mixture was reacted at room temperature for 9 hr. The reaction solution was washed twice with 10% aqueous acetic acid solution (216 g) and twice with ion exchange water (216 g). Magnesium sulfate (manufactured by KANTO CHEMICAL CO., INC.) (12.9 g) was added to the organic layer, and the mixture was stirred for 30 min. Magnesium sulfate was filtered off, and the filtrate was concentrated by an evaporator. The concentrate was re-dissolved in hexane (284 g), the insoluble material was filtered off, and the filtrate was extracted 6 times with acetonitrile (168 g). The acetonitrile layer was recovered and concentrated by an evaporator to give a crude product (17.0 g). The obtained crude product (13.6 g) subjected to column purification to give 4-(D-α-tocopherol hemisuccinyl)phenylacetic acid (3.44 g).

¹H-NMR spectrum (600 MHz, CDCl₃) of 4-(D-α-tocopherol hemisuccinyl)phenylacetic acid δ0.83-0.87 ppm (m, 12H), δ1.02-1.85 ppm (m, 26H), δ1.96 ppm (s, 3H), δ2.01 ppm (s, 3H), δ2.08 ppm (s, 3H), δ2.56-2.59 ppm (t, 2H), δ2.71-2.76 ppm (m, 2H), δ2.92-2.96 ppm (m, 2H), δ3.66 ppm (s, 2H), δ7.05-7.08 ppm (m, 2H), δ7.27-7.31 ppm (m, 2H)

<Synthesis of E-Ph-P4C2> di-4PE form (0.350 g, 0.929 mmol), 4-(D-α-tocopherol hemisuccinyl)phenylacetic acid (1.04 g, 1.95 mmol), and DMAP (0.0454 g, 0.372 mmol) were dissolved in chloroform (10.5 g) at room temperature. Thereto was added EDC (0.534 g, 2.79 mmol), and the mixture was reacted at 30-35° C. for 4 hr. The reaction solution was washed twice with 20% brine (7.00 g) and dehydrated using magnesium sulfate (0.350 g). Magnesium sulfate was filtered off, and the filtrate was concentrated in an evaporator to give a crude product (1.31 g). The obtained crude product was subjected to column purification to give E-Ph-P4C2 (0.860 g).

¹H-NMR spectrum (600 MHz, CDCl₃) of E-Ph-P4C2

δ0.83-0.87 ppm (m, 24H), δ1.02-1.85 ppm (m, 66H), δ1.94-1.98 ppm (m, 10H), δ2.00 ppm (s, 6H), δ2.08 ppm (s, 6H), δ2.53-2.66 ppm (m, 8H), δ2.71-2.85 ppm (m, 8H), δ2.85-2.95 ppm (m, 8H), δ3.65 ppm (s, 4H), δ4.11-4.14 ppm (t, 4H), δ7.05-7.08 ppm (m, 2H), δ7.27-7.31 ppm (m, 2H)

[Example 6] L-Ph-P4C2

L-Ph-P4C2 was synthesized by the same synthetic pathway as in Example 1.

<Acid Anhydridation of Linoleic Acid>

Linoleic acid (manufactured by NOF CORPORATION) (69.6 g, 248 mmol) was dissolved in chloroform (560 g) at room temperature, and the mixture was cooled to 10-15° C. Thereto was added dropwise a suspension of DCC (25.1 g, 121 mmol) dissolved in chloroform (140 g), and the mixture was reacted at 10-25° C. for 2 hr. The reaction solution was filtered, and the filtrate was concentrated by an evaporator. The obtained concentrate was re-dissolved in hexane (210 g), and insoluble material was removed by filtration. The obtained filtrate was concentrated by an evaporator to give linoleic anhydride (63.8 g).

¹H-NMR spectrum (600 MHz, CDCl₃) of linoleic anhydride

δ0.86-0.90 ppm (t, 6H), δ1.25-1.40 ppm (m, 32H), δ1.61-1.68 (m, 4H), δ1.94-2.05 (m, 8H), δ2.39-2.46 (t, 4H), δ5.30-5.38 (m, 8H)

<Synthesis of 4-linoleoyloxyphenylacetic Acid>

Linoleic anhydride (42.8 g, 78.9 mmol) and 4-hydroxyphenylacetic acid (6.00 g, 39.4 mmol) were dissolved in chloroform (647 g). Thereto was added DMAP (1.93 g, 15.8 mmol) and the mixture was reacted at 15-20° C. for 9 hr. The reaction solution was washed twice with 10% aqueous acetic acid solution (216 g) and twice with ion exchange water (216 g). Magnesium sulfate (12.9 g) was added to the organic layer, and the mixture was stirred for 30 min. Magnesium sulfate was filtered off, and the filtrate was concentrated by an evaporator. The concentrate was re-dissolved in hexane (284 g), the insoluble material was filtered off, and the filtrate was extracted 6 times with acetonitrile (168 g). The acetonitrile layer was recovered and concentrated by an evaporator to give a crude product (18.1 g). The obtained crude product (14.5 g) subjected to column purification to give 4-linoleoyloxyphenylacetic acid (3.66 g).

¹H-NMR spectrum (600 MHz, CDCl₃) of 4-linoleoyloxyphenylacetic acid

δ0.77-0.89 (t, 3H), δ1.27-1.42 (m, 4H), δ1.71-1.77 (m, 2H), δ1.99-2.03 (m, 4H), δ2.52-2.56 (m, 2H), δ3.64 (s, 2H), δ5.34-5.39 (m, 4H), δ7.03-7.06 (m, 2H), δ7.28-7.31 (m, 2H)

<Synthesis of L-Ph-P4C2> di-4PE form (0.350 g, 0.929 mmol), 4-linoleoyloxyphenylacetic acid (0.808 g, 1.95 mmol), and DMAP (0.0454 g, 0.372 mmol) were dissolved in chloroform (10.5 g) at room temperature. Thereto was added EDC (0.534 g, 2.79 mmol), and the mixture was reacted at 30-35° C. for 4 hr. The reaction solution was washed twice with 20% brine (7.00 g) and dehydrated using magnesium sulfate (0.350 g). Magnesium sulfate was filtered off, and the filtrate was concentrated in an evaporator to give a crude product (1.02 g). The obtained crude product was subjected to column purification to give L-Ph-P4C2 (0.668 g).

¹H-NMR spectrum (600 MHz, CDCl₃) of L-Ph-P4C2

δ0.87-0.90 (t, 6H), δ1.24-1.41 (m, 38H), δ1.55-1.76 (m, 12H), δ1.93-2.07 (m, 12H), δ2.53-2.56 (m, 4H), δ2.63-2.65 (m, 4H), δ2.77-2.89 (m, 8H), δ3.59 (s, 4H), δ4.11-4.13 (t, 4H), δ5.34-5.39 (m, 8H), δ7.02-7.05 (m, 4H), δ7.26-7.30 (m, 4H)

[Example 7] HD-Ph-P4C2

HD-Ph-P4C2 was synthesized by the same synthetic pathway as in Example 1.

<Acid Anhydridation of 2-Hexyldecanoic Acid>

2-Hexyldecanoic acid (manufactured by Tokyo Chemical Industry Co., Ltd.) (6.36 g, 24.8 mmol) was dissolved in chloroform (560 g) at room temperature, and the mixture was cooled to 10-15° C. Thereto was added dropwise a suspension of DCC (2.51 g, 12.1 mmol) dissolved in chloroform (14 g), and the mixture was reacted at 10-25° C. for 2 hr. The reaction solution was filtered, and the filtrate was concentrated by an evaporator. The obtained concentrate was re-dissolved in hexane (21 g), and insoluble material was removed by filtration. The obtained filtrate was concentrated by an evaporator to give 2-hexyldecanoic anhydride (5.83 g).

¹H-NMR spectrum (600 MHz, CDCl₃) of 2-hexyldecanoic anhydride

δ0.86-0.90 ppm (m, 12H), δ1.25-1.40 ppm (m, 40H), δ1.61-1.68 (m, 8H), δ2.39-2.46 (m, 2H)

<Synthesis of 2-hexyldecanoyloxyphenylacetic Acid>

2-Hexyldecanoic anhydride (3.90 g, 7.89 mmol) and 4-hydroxyphenylacetic acid (0.600 g, 3.94 mmol) were dissolved in chloroform (65 g). Thereto was added DMAP (0.193 g, 1.58 mmol) and the mixture was reacted at room temperature for 9 hr. The reaction solution was washed twice with 10% aqueous acetic acid solution (22 g) and twice with ion exchange water (22 g). Magnesium sulfate (1.5 g) was added to the organic layer, and the mixture was stirred for 30 min. Magnesium sulfate was filtered off, and the filtrate was concentrated by an evaporator. The concentrate was re-dissolved in hexane (28 g), the insoluble material was filtered off, and the filtrate was extracted 6 times with acetonitrile (17 g). The acetonitrile layer was recovered and concentrated by an evaporator to give a crude product (1.64 g). The obtained crude product (1.32 g) was subjected to column purification to give 2-hexyldecanoyloxyphenylacetic acid (0.333 g).

¹H-NMR spectrum (600 MHz, CDCl₃) of 2-hexyldecanoyloxyphenylacetic acid

δ0.77-0.89 (t, 6H), δ1.27-1.42 (m, 20H), δ1.71-1.77 (m, 4H), δ2.52-2.56 (m, 2H), δ3.64 (s, 2H), δ7.03-7.06 (m, 2H), δ7.28-7.31 (m, 2H)

<Synthesis of HD-Ph-P4C2> di-4PE form (0.117 g, 0.310 mmol), 2-hexyldecanoyloxyphenylacetic acid (0.254 g, 0.650 mmol), and DMAP (0.0151 g, 0.124 mmol) were dissolved in chloroform (3.5 g) at room temperature. Thereto was added EDC (0.178 g, 0.930 mmol), and the mixture was reacted at 30-35° C. for 4 hr. The reaction solution was washed twice with 20% brine (3 g) and dehydrated using magnesium sulfate (0.3 g). Magnesium sulfate was filtered off, and the filtrate was concentrated in an evaporator to give a crude product (0.320 g). The obtained crude product was subjected to column purification to give HD-Ph-P4C2 (0.210 g).

¹H-NMR spectrum (600 MHz, CDCl₃) of HD-Ph-P4C2

δ0.87-0.90 (t, 12H), δ1.23-1.41 (m, 40H), δ1.54-1.76 (m, 20H), δ1.93-1.97 (m, 4H), δ2.54-2.57 (m, 2H), δ2.63-2.65 (m, 4H), δ2.81-2.89 (m, 8H), δ3.59 (s, 4H), δ4.11-4.13 (t, 4H), δ7.00-7.02 (m, 4H), δ7.26-7.29 (m, 4H)

[Example 8] O-Ph-amide-P4C2

<Amination of Hydroxyl Group of di-4PE Form> di-4PE form (0.815 g, 2.16 mmol), phthalimide (manufactured by KANTO CHEMICAL CO., INC.) (0.892 g, 6.06 mmol), and triphenylphosphine (manufactured by KANTO CHEMICAL CO., INC.) (1.59 g, 6.06 mmol) were dissolved in dichloromethane (5 g) at room temperature. Thereto was added diisopropyl azodicarboxylate (manufactured by ACROS ORGANICS) (1.05 g, 5.20 mmol), and the mixture was reacted at room temperature for 4 hr. To the reaction solution was added methanol (10 g), and the mixture was concentrated by an evaporator. The concentrate was re-dissolved in methanol (4 g), ethylenediamine.monohydrate (manufactured by KANTO CHEMICAL CO., INC.) (5.08 g, 65.0 mmol) was added, and the mixture was reacted at 35-45° C. for 3 hr. The reaction solution was concentrated by an evaporator, and the concentrate was re-dissolved in 5% aqueous sodium dihydrogen phosphate solution (10 g), and washed 3 times with ethyl acetate (10 g). Thereafter, the aqueous layer was adjusted to pH 12 with aqueous sodium hydroxide solution, extracted twice with dichloromethane (10 g), and dehydrated using sodium sulfate (manufactured by KANTO CHEMICAL CO., INC.) (1 g). Sodium sulfate was filtered off, and the filtrate was concentrated by an evaporator to give di-4PE-amine form (0.572 g).

¹H-NMR spectrum (400 MHz, CDCl₃) of di-4PE-amine form

δ1.20-1.55 ppm (m, 10H), δ1.51-1.54 ppm (m, 4H), δ1.95-2.05 ppm (m, 4H), δ2.58-2.66 ppm (m, 4H), δ2.72 ppm (t, 4H), δ2.78-2.83 ppm (m, 4H), δ2.89-2.92 ppm (m, 4H)

<Synthesis of O-Ph-amide-P4C2> di-4PE-amine form (0.348 g, 0.929 mmol), 4-oleoyloxyphenylacetic acid (0.813 g, 1.95 mmol), and DMAP (0.0454 g, 0.372 mmol) were dissolved in chloroform (10.5 g) at room temperature. Thereto was added EDC (0.534 g, 2.79 mmol), and the mixture was reacted at 30-35° C. for 4 hr. The reaction solution was washed twice with 20% brine (7.00 g) and dehydrated using magnesium sulfate (0.350 g). Magnesium sulfate was filtered off, and the filtrate was concentrated in an evaporator to give a crude product (1.10 g). The obtained crude product was subjected to column purification to give O-Ph-amide-P4C2 (0.629 g).

¹H-NMR spectrum (600 MHz, CDCl₃) of O-Ph-amide-P4C2

δ0.86-0.90 (t, 6H), δ1.22-1.42 (m, 46H), δ1.61-1.77 (m, 12H), δ1.92-2.03 (m, 12H), δ2.52-2.56 (m, 4H), δ2.62-2.66 (m, 4H), δ2.80-2.89 (m, 8H), δ3.22-3.25 (m, 4H), δ3.54 (s, 4H), δ5.32-5.37 (m, 6H), δ7.05-7.05 (m, 4H), δ7.25-7.26 (m, 4H)

[Example 9] O-Ph-C3M

<Synthesis of O-Ph-C3M> bis[{N-methyl-N-(3-hydroxypropyl)amino}ethyl]disulfide (di-MAP form) (0.275 g, 0.929 mmol) synthesized by the method described in patent document 2,4-oleoyloxyphenylacetic acid (0.813 g, 1.95 mmol), and DMAP (0.0454 g, 0.372 mmol) were dissolved in chloroform (10.5 g) at room temperature. Thereto was added EDC (0.534 g, 2.79 mmol), and the mixture was reacted at 30-35° C. for 4 hr. The reaction solution was washed twice with 20% brine (7.00 g) and dehydrated using magnesium sulfate (0.350 g). Magnesium sulfate was filtered off, and the filtrate was concentrated in an evaporator to give a crude product (0.871 g). The obtained crude product was subjected to column purification to give O-Ph-C3M (0.498 g).

¹H-NMR spectrum (600 MHz, CDCl₃) of O-Ph-C3M

δ0.86-0.90 (t, 6H), δ1.22-1.42 (m, 44H), δ1.77-1.82 (m, 8H), δ1.99-2.03 (m, 8H), δ2.26 (s, 6H), δ2.28-2.30 (t, 4H), δ2.52-2.56 (m, 4H), δ2.67-2.69 (m, 4H), δ2.79-2.81 (m, 4H), δ3.54 (s, 4H), δ4.10-4.13 (t, 4H), δ5.32-5.37 (m, 4H), δ7.05-7.05 (m, 4H), δ7.25-7.26 (m, 4H)

[Comparative Example 1] Synthesis of O-P4C2

O-P4C2 was synthesized by the synthetic pathway described in patent document 2.

¹H-NMR spectrum (600 MHz, CDCl₃) of O-P4C2

δ0.86-0.90 (t, 6H), δ1.20-1.35 (m, 40H), δ1.58-1.70 (m, 4H), δ1.75-1.83 (m, 4H), δ1.95-2.05 (m, 8H), δ2.24-2.32 (m, 10H), δ2.66-2.70 (m, 4H), δ2.78-2.82 (m, 4H), δ4.10-4.13 (t, 4H), δ5.13-5.38 (m, 4H)

[Comparative Example 2] Synthesis of E-P4C2

E-P4C2 was synthesized by the synthetic pathway described in patent document 2.
$^1$H-NMR spectrum (400 MHz, CDCl$_3$) of E-P4C2
δ0.83-0.88 (m, 24H), δ1.00-1.81 (m, 66H), δ1.95-2.10 (m, 22H), δ2.55-2.60 (t, 4H), δ2.62-2.66 (m, 4H), δ2.73-2.77 (t, 4H), δ2.80-2.84 (m, 4H), δ2.86-2.95 (m, 8H), δ4.12-4.17 (t, 4H)

[Experimental Example 1] Preparation of mRNA-Encapsulating Particles and Property Evaluation 1. Preparation of mRNA-Encapsulated LNP by Ethanol Dilution Method
(1) Preparation of Ethanol Solution of Lipid A lipid solution in ethanol was prepared by mixing 5 mM cationic lipid, 5 mM phospholipid and 5 mM cholesterol at desired ratios in a 5 mL tube to achieve the total lipid amount of 131.5 nmol, further adding DMG-PEG2k (1 mM ethanol solution) in an amount corresponding to 3% of the total lipid amount, and adding ethanol to achieve a total volume of 30 μL.

(2) Preparation of Acidic Buffer Solution of Nucleic Acid

An acidic buffer solution of nucleic acid was prepared by weighing 3 μg of mRNA solution (concentration varies depending on the efficiency of in vitro translation and is generally 0.6-0.8 μg/μL) in an Eppendorf tube and adding acidic malate buffer (20 mM, pH3.0, containing 30 mM NaCl) to make the total amount 45 μL.

(3) Preparation of LNP by Ethanol Dilution Method

The acidic buffer solution (45 μL) of nucleic acid was added to an ethanol solution (30 μL) of lipid while vortexing. Successively, MES buffer (pH 5.5) (925 μL) was added to the mixture. The total amount of the LNP solution was transferred to Amicon Ultra 4 (Nihon Millipore K.K.) to which MES buffer (1 mL) was added in advance. To the 5 mL tube containing the LNP solution was added 1 mL of MES buffer and washing was performed. The washing was performed twice. After ultrafiltration and concentration to about 100 μL under centrifugation conditions (25° C., 1000 g, 3 min), the volume was increased to 4 mL using PBS, and concentration was performed again under centrifugation conditions (25° C., 1000 g, 10 min). Finally, PBS was used to adjust to the target lipid concentration.

2. Measurement of Particle Size and Surface Potential of Various mRNA-Encapsulated LNPs The particle size and the surface potential were measured by the dynamic light scattering method (Zetasizer Nano; Malvern). The particle size and one example of the surface potential of the various LNPs prepared by the method of the above-mentioned 1. are shown in Tables 3-9.

TABLE 3

| cationic lipid lipid O-Ph-P3C1 of Example 1 | lipid composition cationic lipid/phospholipid/Chol/DMG-PEG2k = 60/10/30/3 | |
|---|---|---|
| particle size (nm) | PdI | zeta potential (mV) |
| 117 | 0.114 | −9.1 |

TABLE 4

| cationic lipid lipid O-Ph-P4C1 of Example 2 | lipid composition cationic lipid/phospholipid/Chol/DMG-PEG2k = 60/10/30/3 | |
|---|---|---|
| particle size (nm) | PdI | zeta potential (mV) |
| 146 | 0.109 | −8.6 |

TABLE 5

| cationic lipid lipid O-Ph-P4C2 of Example 3 | lipid composition cationic lipid/phospholipid/Chol/DMG-PEG2k = 60/10/30/3 | |
|---|---|---|
| particle size (nm) | PdI | zeta potential (mV) |
| 147 | 0.143 | −6.1 |

TABLE 6

| cationic lipid lipid O-P4C2 of Comparative Example 1 | lipid composition cationic lipid/phospholipid/Chol/DMG-PEG2k = 60/10/30/3 | |
|---|---|---|
| particle size (nm) | PdI | zeta potential (mV) |
| 186 | 0.138 | −11.0 |

TABLE 7

| cationic lipid lipid O-Ph-P4C2 of Example 3 | lipid composition cationic lipid/phospholipid/Chol/DMG-PEG2k = 52.5/7.5/40/3 | |
|---|---|---|
| particle size (nm) | PdI | zeta potential (mV) |
| 84 | 0.091 | −3.3 |

TABLE 8

| cationic lipid lipid O-Bn-P4C2 of Example 4 | lipid composition cationic lipid/phospholipid/Chol/DMG-PEG2k = 52.5/7.5/40/3 | |
|---|---|---|
| particle size (nm) | PdI | zeta potential (mV) |
| 90 | 0.097 | −3.7 |

TABLE 9

| cationic lipid lipid O-P4C2 of Comparative Example 1 | lipid composition cationic lipid/phospholipid/Chol/DMG-PEG2k = 52.5/7.5/40/3 | |
|---|---|---|
| particle size (nm) | PdI | zeta potential (mV) |
| 80 | 0.105 | −2.9 |

3. Results

All LNPs showed a preferable form of particle size 30-300 nm, and electric charge (zeta potential) at physiological pH of preferable form of −15-+15 mV.

[Experimental Example 2] Preparation of siRNA-Encapsulated Particles and Property Evaluation 1. Preparation of siRNA-Encapsulated LNP by Micro Flow Path Method (1) Preparation of Ethanol Solution of Lipid A lipid solution in ethanol was prepared by mixing 5 mM cationic lipid and 5 mM cholesterol at desired ratios in an Eppendorf tube to achieve the total lipid amount of 900 nmol, further adding DMG-PEG2k (2 mM ethanol solution) in an amount corresponding to 1.5% of the total lipid amount, and adding ethanol to achieve a total volume of 100 μL.

(2) Preparation of Acidic Buffer Solution of Nucleic Acid

An acidic buffer solution of nucleic acid was prepared by weighing 4.5 μg of siRNA solution (4 mg/mL) in a 5 mL tube and adding acidic malate buffer (20 mM, pH3.0) to make the total amount 900 μL.

(3) Preparation of LNP Using Micro Flow Path

The acidic buffer solution of nucleic acid and the ethanol solution of lipid were each weighed in a syringe. Using an ultra high-speed nanomedicament producing apparatus NanoAssmblr (manufactured by Precision NanoSystems), LNP was prepared under the conditions of nucleic acid solution 18 mL/min, lipid solution 2 mL/min, syringe holder temperature 30° C., and collected in a 15 mL tube. PBS (3000 μL) was added to the 15 mL tube, transferred to Amicon Ultra 4, and ultrafiltration and concentration were performed to about 100 μL under centrifugation conditions (30° C., 1000 g, 6 min). Thereafter, the volume was increased to 4 mL using PBS, and concentration was performed again under centrifugation conditions (30° C., 1000 g, 6 min). Finally, PBS was used to adjust to the target lipid concentration.

2. Measurement of Particle Size and Surface Potential of Various siRNA-Encapsulated LNPs The particle size and the surface potential were measured by the dynamic light scattering method. The particle size and one example of the surface potential of the various LNPs prepared by the method described in [Experimental Example 5], 1, are shown in Tables 10-12.

TABLE 10

| cationic lipid lipid O-Ph-P4C2 of Example 3 | lipid composition cationic lipid/Chol/ DMG-PEG2k = 70/30/1.5 | |
| --- | --- | --- |
| particle size (nm) | PdI | zeta potential (mV) |
| 96 | 0.079 | −6.03 |

TABLE 11

| cationic lipid lipid O-Bn-P4C2 of Example 4 | lipid composition cationic lipid/Chol/ DMG-PEG2k = 70/30/1.5 | |
| --- | --- | --- |
| particle size (nm) | PdI | zeta potential (mV) |
| 98 | 0.069 | −6.45 |

TABLE 12

| cationic lipid lipid O-P4C2 of Comparative Example 1 | lipid composition cationic lipid/Chol/ DMG-PEG2k = 70/30/1.5 | |
| --- | --- | --- |
| particle size (nm) | PdI | zeta potential (mV) |
| 98 | 0.099 | −7.00 |

3. Results

All LNPs showed a preferable form of particle size 30-300 nm, and electric charge (zeta potential) at physiological pH of preferable form of −10-+10 mV.

[Experimental Example 3] Measurement of Liposomal pKa

1. Preparation of Various LNPs

For the evaluation of Liposomal pKa, empty LNP not encapsulating nucleic acid was used. The empty LNP (cationic lipid: DOPC:Chol:DMP-PEG2k=60:10:30:3) was produced by performing particle preparation in the method described in [Experimental Example 1] without using a nucleic acid.

2. Measurement of Liposomal pKa 20 mM Citrate buffer, sodium phosphate buffer and tris HCl buffer each containing NaCl at a final concentration of 150 mM and adjusted to various pHs within the range of pH 3.0-10.0 were prepared. LNP prepared in [Experimental Example 3], 1, was diluted with PBS to a lipid concentration of 0.5 mM. TNS (manufactured by Sigma) was diluted with ultrapure water to 0.6 mM. TNS solution (2 μL), various LNP solutions (12 μL), and buffers adjusted to various pHs (186 μL) were added to a black 96 well plate. The plate was protected from light and shaken at 400 rpm for 10 min. The fluorescence intensity (excitation: 321 nm/emission: 447 nm) was measured using a plate reader (manufactured by TECAN). The relative fluorescence intensity was calculated as a percentage, with the maximum value of the fluorescence intensity in each LNP being 100% and the minimum value being 0%. Furthermore, the pH at which the relative fluorescence intensity was 50% was taken as Liposomal pKa. The evaluation results of the Liposomal pKa of various LNPs are shown in Table 13.

TABLE 13

| cationic lipid_LNP | Liposomal pKa |
| --- | --- |
| lipid (O-Ph-P3C1) of Example 1 | 5.5 |
| lipid (O-Ph-P4C1) of Example 2 | 6.1 |
| lipid (O-Ph-P4C2) of Example 3 | 6.1 |
| lipid (O-P4C2) of Comparative Example 1 | 5.9 |

3. Results

All LNPs showed Liposomal pKa within the pKa range (5.5-7.2) preferable for endosomal escape. In addition, the Liposomal pKa of LNP could be adjusted by modifying the peripheral structure of amino group of cationic lipid.

[Experimental Example 4] Evaluation of Hemolysis Activity (Membrane Fusion Capacity) at pH 7.4 and pH 5.5

1. Adjustment of Various LNPs

For the evaluation of hemolysis activity, empty LNP not encapsulating nucleic acid was used. The empty LNP was produced by performing particle preparation in the method described in [Experimental Example 2], 1, without using a nucleic acid.

2. Obtainment of Mouse Erythrocyte 6-7-Week-old male ICR mice were euthanized, and about 1000 μL of blood was collected from the inferior vena cava. The obtained blood was immediately mixed with 0.5 μL of heparin solution (5000 U/5 mL). About 9 ml of PBS was added to the blood to make the total amount 10 mL, and after mixing by inversion, centrifugation was performed (4° C., 400 g, 10 min). The supernatant containing plasma components was removed with a Pasteur pipette. About 9 mL of PBS was added to the blood cell components to make the total amount 10 mL, and centrifugation was performed again. Similar washing operation was repeated 4 times to obtain mouse erythrocytes.

3. Evaluation of Hemolysis Activity

Mouse erythrocytes were measured by 2, 4, 6, 8, 10 μL, and diluted with PBS containing 1% (w/v) Triton-X100. The whole amount was transferred to a transparent 96 well plate, and the absorbance at 545 nm was measured using a plate reader. An analytical curve was prepared using this dilution series, and the point at which the absorbance was 1 was determined as the blood cell volume to be used in the hemolysis assay. An empty LNP solution was weighed in an Eppendorf tube, diluted with malic acid-PBS buffer (pH 5.5, pH 6.5, pH 7.4), and mouse erythrocytes were further added. The final concentration of lipid was set to 100 μM, and the final volume of the solution was set to 250 μL. Each tube was shaken at 1900 rpm for 30 min. Each sample was centrifuged under centrifugation conditions (4° C., 400 g, 5 min), the supernatant (200 μL) was transferred to a transparent 96 well plate, and the absorbance at 545 nm was measured. As a negative control, untreated erythrocytes were used. As a positive control, 1% (w/v) Triton-X was used. The absorbance of each sample was normalized by negative control and positive control.

4. Results

The results are shown in FIG. 1. A higher value means higher membrane fusion capacity (hemolysis activity). LNP (O-Ph-P4C2_LNP) using the cationic lipid of the present invention did not show hemolysis activity at physiological pH (7.4). On the other hand, it showed high hemolysis activity of not less than 80% at endosomal environment pH (5.5).

[Experimental Example 5] Evaluation of Hemolysis Activity of Various LNPs at pH 5.5

1. Adjustment of Various LNPs

An empty LNP was produced by performing particle preparation in the method described in [Experimental Example 2], 1, without using a nucleic acid.

2. Obtainment of Mouse Erythrocyte

Mouse erythrocytes were obtained by the method described in "Experimental Example 4".

3. Evaluation of Hemolysis Activity

Mouse erythrocytes were measured by 2, 4, 6, 8, 10 μL, and diluted with PBS containing 1% (w/v) Triton-X100. The whole amount was transferred to a transparent 96 well plate, and the absorbance at 545 nm was measured using a plate reader. An analytical curve was prepared using this dilution series, and the point at which the absorbance was 1 was determined as the blood cell volume to be used in the hemolysis assay. An empty LNP solution was weighed in an Eppendorf tube, diluted with malic acid-PBS buffer (pH 5.5), and mouse erythrocytes were further added. The final concentration of lipid was set to 1.56, 6.25, 25, 100, 400 μM, and the final volume of the solution was set to 250 μL. Each tube was shaken at 1900 rpm for 30 min. Each sample was centrifuged under centrifugation conditions (4° C., 400 g, 5 min), the supernatant (200 μL) was transferred to a transparent 96 well plate, and the absorbance at 545 nm was measured. As a negative control, untreated erythrocytes were used. As a positive control, a sample added with 1% (w/v) Triton-X100 was used. The absorbance of each sample was normalized by negative control and positive control.

4. Results

Figure 2:
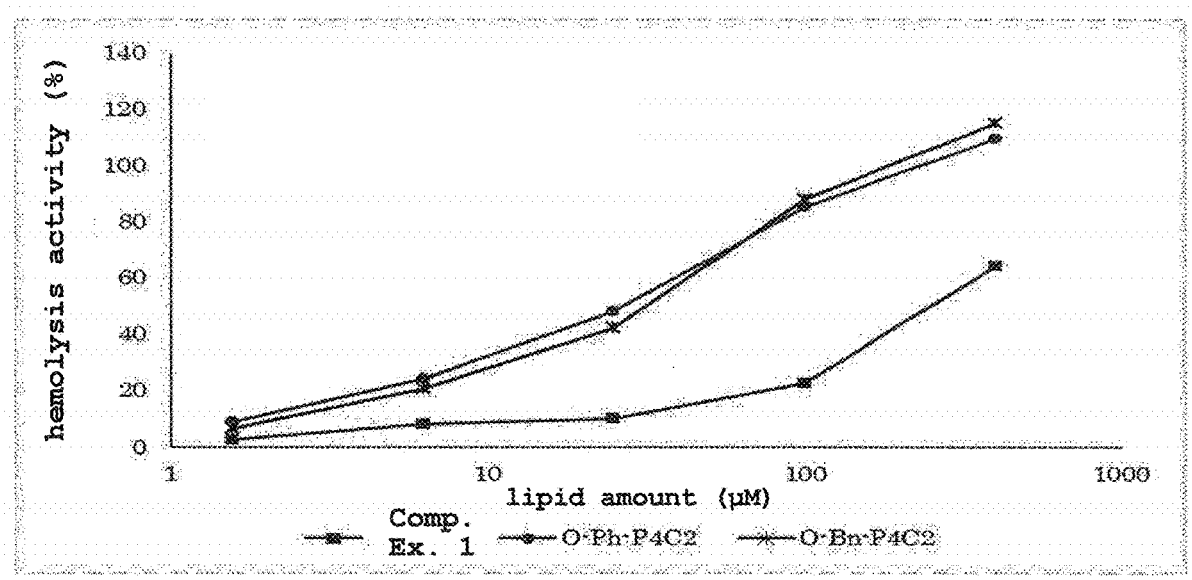
FIG. 2 shows the hemolysis activity at various lipid concentrations and pH 5.5 of various LNPs prepared from the cationic lipid of the present invention (O-Ph-P4C2 and O-Bn-P4C2) and Comparative Example 1.

The results are shown in FIG. 2. A higher value means higher membrane fusion capacity (hemolysis activity). LNP (O-Ph-P4_C2_LNP) and O-Bn-P4C2_LNP) using the cationic lipid of the present invention both showed higher hemolysis activity at various lipid concentrations than LNP of Comparative Example 1. O-Ph-P4C2_LNP and O-Bn-P4C2_LNP did not show difference in the hemolysis activity. High hemolysis activity at pH 5.5 means high interaction with the endosome membrane in the endosomal environment, that is, high efficiency of escape from endosome. The LNPs (O-Ph-P4C2_LNP and O-Bn-P4C2_LNP) using the cationic lipid of the present invention have high hemolysis activity, indicating that they are superior in endosomal escape.

[Experimental Example 6] Evaluation 1 of Gene Expression In Vitro

1. Preparation of Various LNPs

LNP encapsulating mRNA that expresses luciferase (cationic lipid:DOPC:Chol=60:10:30) was prepared by the method described in [Experimental Example 1], 1.

2. Time-Course Evaluation of Gene Expression In Vitro

Human kidney cancer cells OSRC2 were seeded in a 3.5 cm dish at $1.0 \times 10^4$ cells/2 mL/Dish 24 hr before transfection. After 24 hr, the medium was exchanged with a culture medium (RPMI1640) containing 0.1 mM D-luciferin. Prepared mRNA-encapsulated LNP was diluted with PBS such that the concentration of mRNA was 6 μg/mL. The diluted mRNA-encapsulated LNP solution (33 μL, mRNA 0.2 μg) was added to the 3.5 cm dish and set in an incubator luminometer KronosDio (manufactured by ATTO). The luminescence intensity of luciferase was measured for 2 min every one hour. The cumulative luminescence intensity for 24 hr was calculated from the obtained time change of expression.

3. Results

Figure 3:
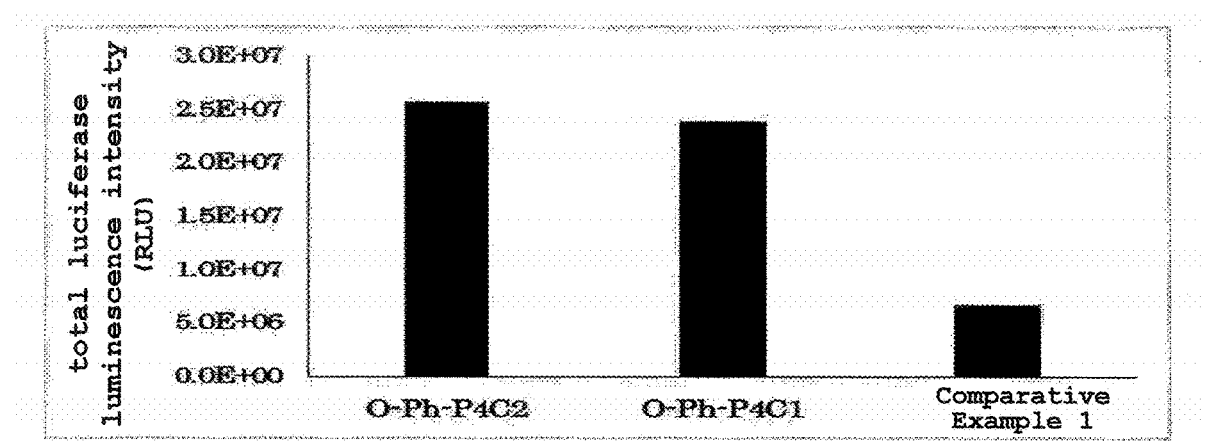
FIG. 3 shows the gene expression activity in vitro of various LNPs prepared from the cationic lipid of the present invention (O-Ph-P4C1, O-Ph-P4C2) and Comparative Example 1.

The results are shown in FIG. 3. A higher value, i.e., higher total luciferase activity, means higher gene expression. LNPs (O-Ph-P4C1_LNP and O-Ph-P4C2_LNP) using the cationic lipid of the present invention showed higher gene expression than LNP (O-P4C2_LNP) using the cationic lipid of Comparative Example 1.

[Experimental Example 7] Evaluation 2 of Gene Expression In Vitro

1. Preparation of Various LNPs

LNP encapsulating mRNA that expresses luciferase (cationic lipid:DOPC:Chol=52.5:7.5:40) was prepared by the method described in [Experimental Example 1], 1.

2. Time-Course Evaluation of Gene Expression In Vitro

Figure 4:
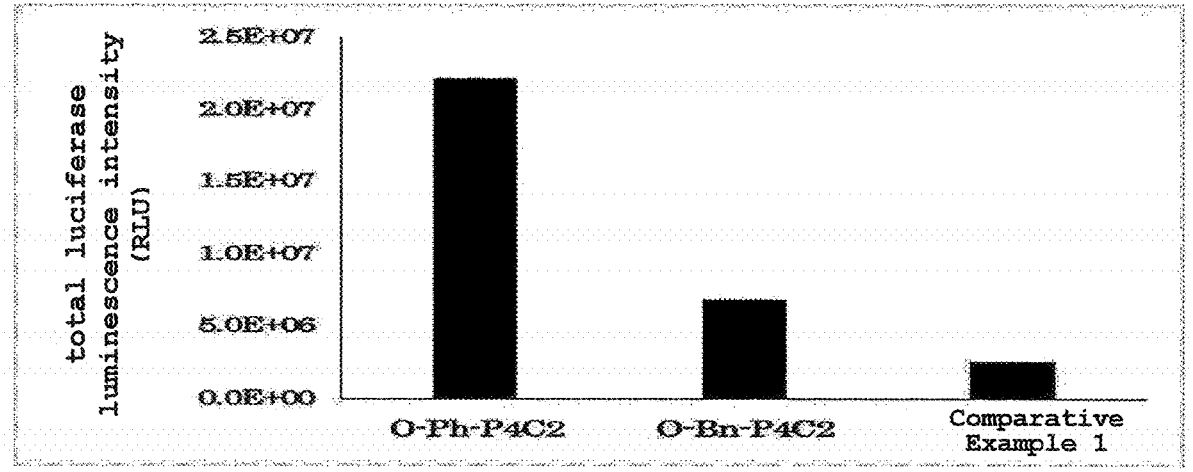
FIG. 4 shows the gene expression activity in vitro of various LNPs prepared from the cationic lipid of the present invention (O-Ph-P4C2 and O-Bn-P4C2) and Comparative Example 1.

Mouse colon cancer cells CT26 were seeded in a 3.5 cm dish at $8.0 \times 10^4/2$ mL/Dish 24 hr before transfection. After 24 hr, the medium was exchanged with a culture medium containing 0.1 mM D-luciferin. Prepared mRNA-encapsulated LNP was diluted with PBS such that the concentration of mRNA was 6 µg/mL. The diluted mRNA-encapsulated LNP solution (67 µL, mRNA 0.4 µg) was added to the 3.5 cm dish and set in an incubator luminometer KronosDio. The luminescence intensity of luciferase was measured for 2 min every one hour. The cumulative luminescence intensity for 24 hr was calculated from the obtained time change of expression.
3. Results The results are shown in FIG. 4. A higher value, i.e., higher total luciferase activity, means higher gene expression. LNPs (O-Ph-P4C2_LNP and O-Bn-P4C2_LNP) using the cationic lipid of the present invention showed higher gene expression activity than LNP of Comparative Example 1. Particularly, O-Ph-P4C2_LNP showed about 10-fold higher gene expression activity than LNP of Comparative Example 1, and it is clear that the LNP has a superior mRNA delivery ability in vitro.

[Experimental Example 8] Time-Course Evaluation of Gene Expression In Vivo

1. Preparation of Various LNPs

LNP encapsulating mRNA that expresses erythropoietin (cationic lipid:DOPC:Chol=52.5:7.5:40) was prepared by the method described in [Experimental Example 1].
2. Time-Course Evaluation of Gene Expression In Vivo The prepared mRNA-encapsulated LNP was diluted with PBS such that the concentration of mRNA was 5 µg/mL. The diluted mRNA-encapsulated LNP was administered into the tail vein of 6-week-old female Balb/c mice at 10 µL per 1 g body weight (0.05 mg/kg as dose of mRNA). The blood (15 µL) was collected from the tail vein of the mice 0.5, 1, 2, 3, 6, 9, 24 hr after the administration. The collected blood was immediately mixed with 0.3 µL of heparin solution (5000 U/5 mL). Each blood sample was centrifuged under centrifugation conditions (25° C., 2000 g, 20 min), and the supernatant was recovered. The concentration of erythropoietin in the supernatant was measured using Mouse Erythropoietin Quantikine ELISA Kit (manufactured by R&D Systems) and by the method described in the protocol of the Kit.
3. Preparation of mRNA-TransIT Complex Using Commercially Available Gene Transfer Reagent TransIT (Registered Trade Mark)

Figure 5:
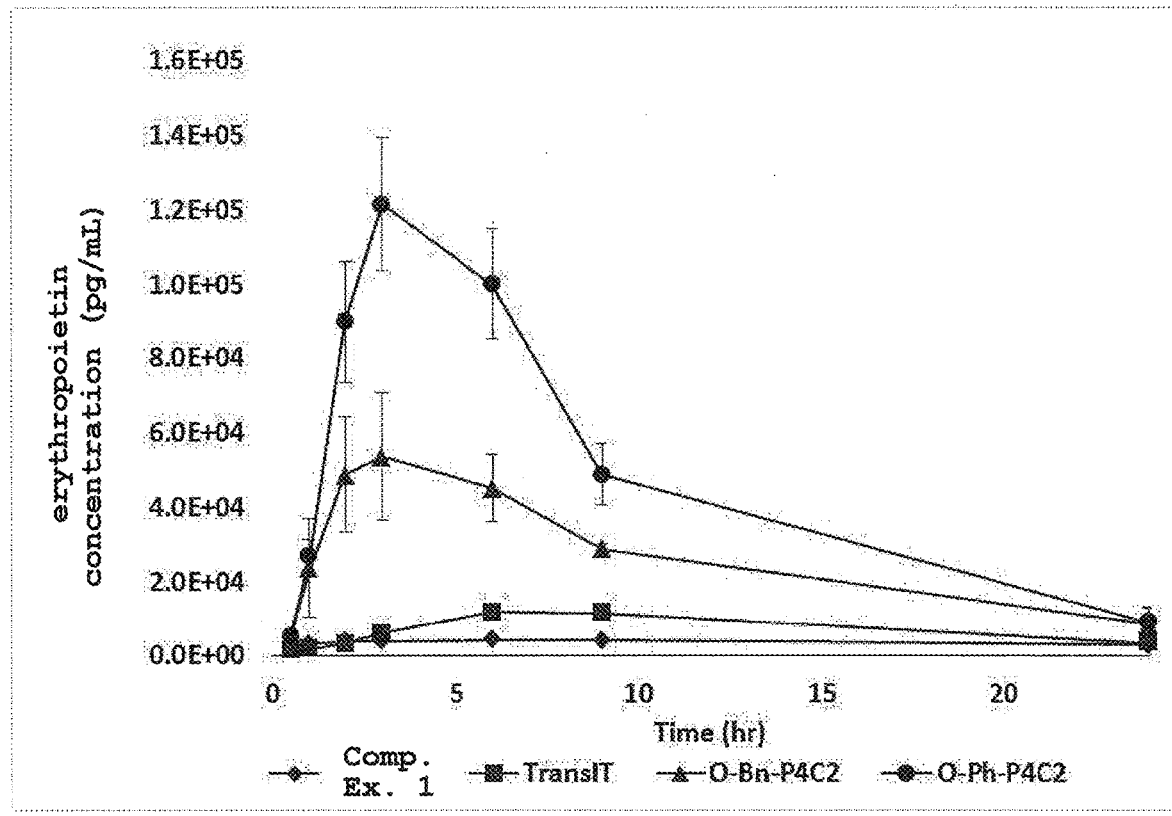
FIG. 5 shows the gene expression activity in vivo of various LNPs prepared from the cationic lipid of the present invention (O-Ph-P4C2 and O-Bn-P4C2) and Comparative Example 1, and commercially available gene transfer reagent TransIT (registered trade mark).

This complex was prepared with reference to a literature (Thess A et al. Molecular Therapy. 2017). The mRNA solution was weighed in an Eppendorf tube such that mRNA was 5 µg. The mRNA solution was diluted with Dulbecco's modified Eagle medium (High-Glucose) to 491 µL. An mRNA-TransIT complex was prepared by adding 5.5 µL of TransIT-mRNA reagent and 3.5 µL of mRNA Boost reagent to the mixture and incubating the mixture for 2 min.
4. Time-Course Evaluation of Gene Expression of mRNA-TransIT Complex In Vivo The gene expression activity was evaluated with reference to a literature (Thess A et al. Molecular Therapy. 2017). The prepared mRNA-TransIT complex was intraperitoneally administered to female 6-week-old Balb/c mice at 5 µL per 1 g body weight (0.05 mg/kg as dose of mRNA). The blood was collected from the tail vein of the mouse at various time points and the erythropoietin concentration was quantified by the method described in [Experimental Example 7], 2.
5. Results The results are shown in FIG. 5. A higher value, i.e., higher erythropoietin activity, means higher gene expression. LNPs (O-Ph-P4C2_LNP and O-Bn-P4C2_LNP) using the cationic lipid of the present invention both showed higher gene expression activity than a commercially available gene transfer reagent (TransIT (registered trade mark)). Particularly, O-Ph-P4C2_LNP showed about 10-fold higher gene expression activity than commercially available gene transfer reagents, and it is clear that the LNP has a superior mRNA delivery ability in vivo.

[Experimental Example 9] Evaluation of Gene Knockdown Activity in Vivo (Delivery of siRNA to Liver)

1. Preparation of Various LNPs

Figure 6:
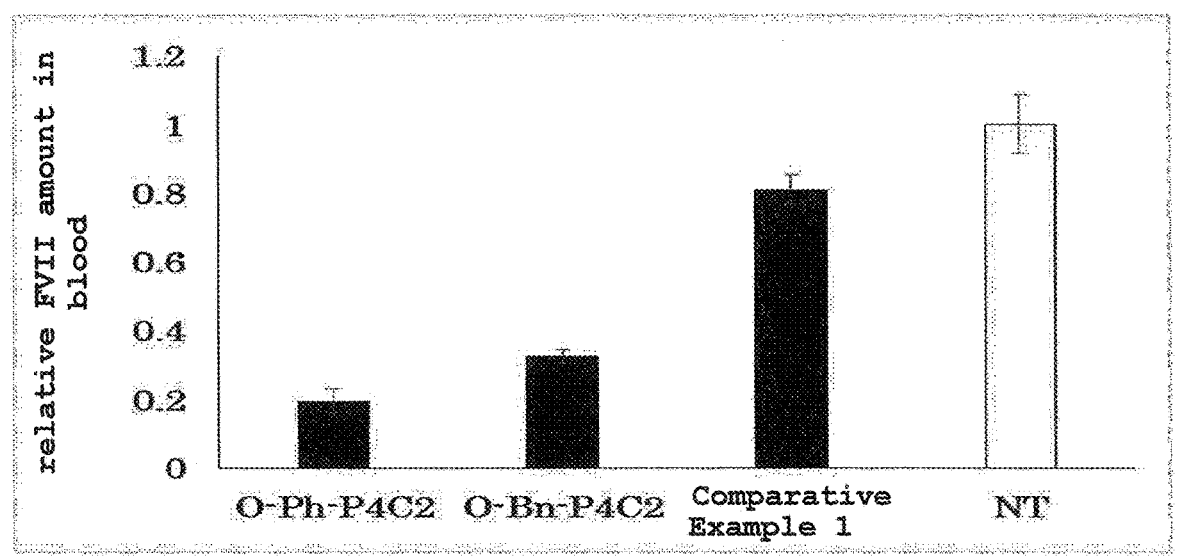
FIG. 6 shows the FVII gene knockdown activity in vivo of various LNPs prepared from the cationic lipid of the present invention (O-Ph-P4C2, O-Bn-P4C2) and Comparative Example 1.

A siRNA-encapsulated LNP to coagulation factor VII (FVII), which is a liver specific protein, was prepared by the method described in [Experimental Example 2], 1.
2. Evaluation of Gene Knockdown Activity in Liver In Vivo The prepared siRNA-encapsulated LNP was diluted with PBS to a siRNA concentration of 2 µg/mL. The diluted siRNA-encapsulated LNP was administered into the tail vein of 4-week-old male ICR mice at 10 µL per 1 g body weight (0.02 mg/kg as dose of siRNA). The mice were euthanized 24 hr later, and about 500 µL of blood was collected from the inferior vena cava. The obtained blood was immediately mixed with 0.5 µL of heparin solution (5000 U/5 mL), and preserved on ice until assay. The blood FVII concentration was measured using Biophen VII assay kit (Aniara) and by the method described in the protocol of the Kit. The blood concentration of FVII in 24 hr after administration of each sample was normalized by the blood FVII concentration of untreated mice.
3. Results The results are shown in FIG. 6. A lower value, i.e., lower expression activity of FVII protein, means higher gene knockdown activity. LNP (O-Ph-P4C2_LNP and O-Bn-P4C2_LNP) using the cationic lipid of the present invention both showed higher gene knockdown activity than LNP of Comparative Example 1. Particularly, it is clear that O-Ph-P4C2_LNP has a superior siRNA delivery ability in vivo.

[Experimental Example 10] Preparation of mRNA-Encapsulated Particles and Property Evaluation 1. Preparation of mRNA-Encapsulated LNP by Micro Flow Path Method
(1) Preparation of Ethanol Solution of Lipid A lipid solution in ethanol was prepared by mixing 5 mM cationic lipid, 5 mM phospholipid and 5 mM cholesterol at desired ratios in a 5 mL tube to achieve the total lipid amount of 2550 nmol, further adding DMG-PEG2k (1 mM ethanol solution) in an amount corresponding to 1.5% of the total lipid amount, and adding ethanol to achieve a total volume of 510 µL.
(2) Preparation of Acidic Buffer Solution of Nucleic Acid An acidic buffer solution of nucleic acid was prepared by weighing 10.8 µg of mRNA solution (concentration varies depending on the efficiency of in vitro translation and is generally 0.6-0.8 µg/µL) in a 5 mL tube and adding acidic malate buffer (20 mM, pH3.0, containing 30 mM NaCl) to make the total amount 1300 µL.
(3) Preparation of LNP preparation using micro flow path The acidic buffer solution of nucleic acid and the ethanol solution of lipid were each weighed in a syringe. Using an ultra high-speed nanomedicament producing apparatus NanoAssmblr, LNP was prepared under the conditions of nucleic acid solution 3 mL/min, lipid solution 1 mL/min, and 1.2 mL thereof was collected in a 15 mL tube. 20 mM MES at pH6.5 (prepared with NaOH) (3000 μL) was added to the 15 mL tube, transferred to Amicon Ultra 4, centrifugation (25° C., 1000 g, 3 min) was repeated, and ultrafiltered and concentrated to about 300 μL by centrifugation. Thereafter, the volume was increased to 4 mL using PBS, and concentrated by repeating centrifugation (25° C., 1000 g, 3 min) again. Finally, PBS was used to adjust to the target lipid concentration.

2. Measurement of Particle Size and Surface Potential of Various mRNA-Encapsulated LNPs The particle size and the surface potential were measured by the dynamic light scattering method. The particle size and one example of the surface potential of the various LNPs prepared by the method of the above-mentioned 1. are shown in Tables 14-21.

TABLE 14

| cationic lipid<br>lipid O-Ph-P4C2 of<br>Example 3 | lipid composition<br>cationic lipid/phospholipid/Chol/DMG-<br>PEG2k = 52.5/7.5/40/1.5 | |
|---|---|---|
| particle size (nm) | PdI | zeta potential (mV) |
| 63 | 0.050 | −5.2 |

TABLE 15

| cationic lipid<br>lipid E-Ph-P4C2 of<br>Example 5 | lipid composition<br>cationic lipid/phospholipid/Chol/DMG-<br>PEG2k = 52.5/7.5/40/1.5 | |
|---|---|---|
| particle size (nm) | PdI | zeta potential (mV) |
| 72 | 0.074 | −7.2 |

TABLE 16

| cationic lipid<br>lipid L-Ph-P4C2 of<br>Example 6 | lipid composition<br>cationic lipid/phospholipid/Chol/DMG-<br>PEG2k = 52.5/7.5/40/1.5 | |
|---|---|---|
| particle size (nm) | PdI | zeta potential (mV) |
| 69 | 0.059 | −6.4 |

TABLE 17

| cationic lipid<br>lipid HD-Ph-P4C2 of<br>Example 7 | lipid composition<br>cationic lipid/phospholipid/Chol/DMG-<br>PEG2k = 52.5/7.5/40/1.5 | |
|---|---|---|
| particle size (nm) | PdI | zeta potential (mV) |
| 61 | 0.074 | −6.2 |

TABLE 18

| cationic lipid<br>lipid O-Ph-P4C2 +<br>O-Ph-amide-<br>P4C2 of<br>Examples 3 and 8 | lipid composition<br>cationic lipid/phospholipid/Chol/DMG-<br>PEG2k = 52.5/7.5/40/1.5<br>cationic lipid = O-Ph-P4C2/O-Ph-amide-<br>P4C2 = 40/12.5 | |
|---|---|---|
| particle size (nm) | PdI | zeta potential (mV) |
| 68 | 0.062 | 2.6 |

TABLE 19

| cationic lipid<br>lipid E-Ph-P4C2 of<br>Example 5 | lipid composition<br>cationic lipid/DOPE/Chol/DMG-<br>PEG2k = 60/30/10/3 | |
|---|---|---|
| particle size (nm) | PdI | zeta potential (mV) |
| 83 | 0.120 | −3.9 |

TABLE 20

| cationic lipid<br>lipid O-P4C2 of<br>Comparative Example 1 | lipid composition<br>cationic lipid/DOPC/Chol/DMG-<br>PEG2k = 52.5/7.5/40/1.5 | |
|---|---|---|
| particle size (nm) | PdI | zeta potential (mV) |
| 63 | 0.068 | −5.8 |

TABLE 21

| cationic lipid<br>lipid E-P4C2 of<br>Comparative Example 2 | lipid composition<br>cationic lipid/DOPE/Chol/DMG-<br>PEG2k = 60/30/10/3 | |
|---|---|---|
| particle size (nm) | PdI | zeta potential (mV) |
| 93 | 0.124 | −2.2 |

3. Results

All LNPs showed a preferable form of particle size 30-300 nm, and electric charge (zeta potential) at physiological pH of preferable form of −15-+15 mV.

[Experimental Example 11] Measurement of Liposomal pKa

1. Preparation of Various LNPs

For the evaluation of Liposomal pKa, empty LNP not encapsulating nucleic acid was used. The empty LNP (cationic lipid:DOPC:Chol:DMG-PEG2k=52.5:7.5:40:1.5) was produced by performing particle preparation in the method described in [Experimental Example 10] without using a nucleic acid.

2. Measurement of Liposomal pKa

Liposomal pKa was calculated by the method described in [Experimental Example 3]. The liposomal pKa values of various LNPs are shown in Table 22.

TABLE 22

| cationic lipid_LNP | Liposomal pKa |
|---|---|
| lipid of Example 3 (O-Ph-P4C2) | 6.4 |
| lipid of Example 5 (E-Ph-P4C2) | 6.4 |
| lipid of Example 6 (L-Ph-P4C2) | 6.3 |
| lipid of Example 7 (HD-Ph-P4C2) | 6.0 |
| lipids of Examples 3 and 8 (O-Ph-<br>P4C2 + O-Ph-amide-P4C2) | 6.5 |
| lipid of Comparative Example 1 (O-P4C2) | 6.0 |

3. Results

All LNPs showed Liposomal pKa within the pKa range (5.5-7.2) preferable for endosomal escape. Addition of O-Ph-amide-P4C2 improved pKa.

[Experimental Example 12] Evaluation of Hemolysis Activity (Membrane Fusion Capacity) at pH 7.4 and pH 5.5

1. Adjustment of Various LNPs

For the evaluation of hemolysis activity, empty LNP not encapsulating nucleic acid was used. The empty LNP was produced by the method described in [Experimental Example 11], 1.

2. Obtainment of Mouse Erythrocyte

Mouse erythrocytes were obtained by the method described in [Experimental Example 4], 2.

3. Evaluation of Hemolysis Activity

Hemolysis activity was evaluated by the method described in [Experimental Example 4], 3.

4. Results

Figure 7:
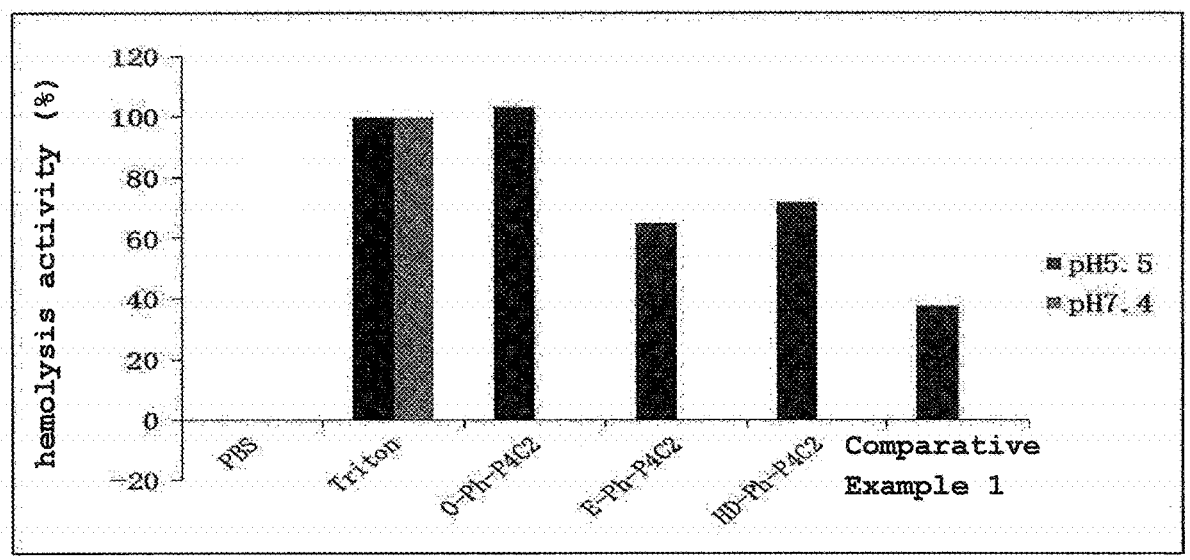
FIG. 7 shows the hemolysis activity (membrane fusion capacity) at pH 7.4 and pH 5.5 of various LNPs prepared from the cationic lipid of the present invention (O-Ph-P4C2, E-Ph-P4C2, HD-Ph-P4C2, O-Ph-amide-P4C2) and Comparative Example 1.

The results are shown in FIG. 7. LNPs using the cationic lipid of the present invention or cationic lipid of Comparative Example 1 did not show hemolysis activity at physiological pH (7.4). On the other hand, it is clear that LNPs using the cationic lipid of the present invention show superior hemolysis activity than LNP using the cationic lipid of Comparative Example 1 at endosomal environment pH (5.5).

[Experimental Example 13] Evaluation 3 of Gene Expression In Vitro

1. Preparation of Various LNPs

LNP encapsulating mRNA that expresses luciferase (cationic lipid:DOPC:Chol=52.5:7.5:40) was prepared by the method described in [Experimental Example 10], 1.

2. Time-Course Evaluation of Gene Expression In Vitro

HeLa cells which are human cervical cancer cells were seeded in a 3.5 cm dish at $5.0 \times 10^4$ cells/2 mL/Dish 24 hr before transfection. After 24 hr, the medium was exchanged with a culture medium (D-MEM) containing 0.1 mM D-luciferin. Prepared mRNA-encapsulated LNP was diluted with PBS such that the concentration of mRNA was about 8 μg/mL. The diluted mRNA-encapsulated LNP solution (about 50 μL, mRNA 0.4 μg) was added to the 3.5 cm dish and set in an incubator luminometer KronosDio. The luminescence intensity of luciferase was measured for 2 min every one hour. The cumulative luminescence intensity for 24 hr was calculated from the obtained time change of expression.

3. Results

Figure 8:
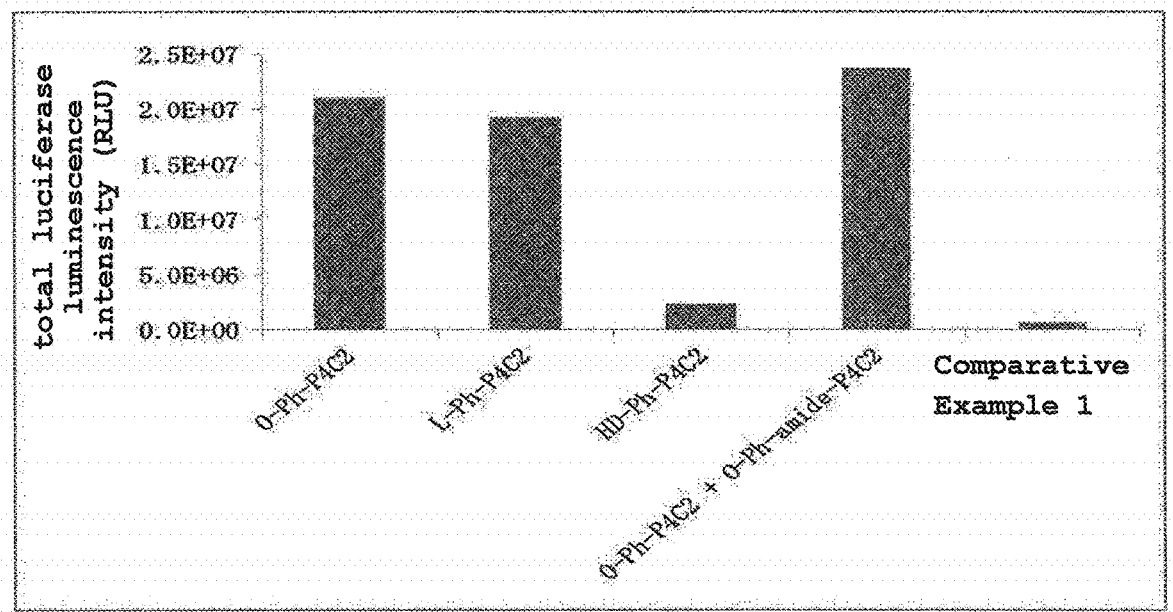
FIG. 8 shows the gene expression activity in vitro of various LNPs prepared from the cationic lipid of the present invention (O-Ph-P4C2, L-Ph-P4C2, HD-Ph-P4C2, O-Ph-amide-P4C2) and Comparative Example 1.

The results are shown in FIG. 8. A higher value, i.e., higher total luciferase activity, means higher gene expression. LNPs (O-Ph-P4C2_LNP, L-Ph-P4C2_LNP, HD-Ph-P4C2_LNP, O-Ph-P4C2+O-Ph-amide-P4C2_LNP, and L-Ph-P4C2_LNP) using the cationic lipid of the present invention showed higher gene expression than LNP (O-P4C2_LNP) using the cationic lipid of Comparative Example 1. Furthermore, O-Ph-P4C2_LNP and O-Ph-P4C2+O-Ph-amide-P4C2_LNP showed higher gene expression activity than commercially available mRNA introduction reagents.

[Experimental Example 14] Evaluation 4 of Gene Expression In Vitro

1. Preparation of LNP

LNP encapsulating mRNA that expresses luciferase (O-Ph-P4C2:DOPC:Chol:DMG-PEG2k=52.5:7.5:40:0.75) was prepared by a method similar to the method described in [Experimental Example 10], 1.

2. Preparation of Lipofectamine-mRNA Complex Using Gene Transfer Reagent (Lipofectamine MessengerMAX)

This complex was prepared according to the protocol of the manufacturer. Opti-MEM medium (125 μL) and Lipofectamine MessengerMAX reagent (7.5 μL) were added into an Eppendorf tube, and incubated for 10 min. A solution of mRNA 2.5 μg/Opti-MEM medium 125 μL was prepared in another Eppendorf tube. Thereto was added 125 μL of the incubated Lipofectamine solution and the mixture was incubated for 5 min to prepare Lipofectamine-mRNA complex.

3. Time-Course Evaluation of Gene Expression In Vitro

Jurkat cells which are human leukemia T cells were seeded in a 3.5 cm dish at $2.0 \times 10^5$ cells/1.8 mL/Dish 24 hr before transfection. After 24 hr, a medium (RPMI1640) containing D-luciferin was added to each dish by 200 μL such that the final concentration was 0.1 mM. mRNA-encapsulated LNP solutions prepared at various concentrations were added by 80 μL (0.4, 0.8, 1.6, 3.2 μg as mRNA), or Lipofectamine-mRNA complex was added by 40, 80, 160, 320 μL (0.4, 0.8, 1.6, 3.2 μg as mRNA), and the dish was set in an incubator luminometer KronosDio. The luminescence intensity of luciferase was measured for 2 min every 3 hours. The cumulative luminescence intensity for 48 hr was calculated from the obtained time change of expression.

4. Results

Figure 9:
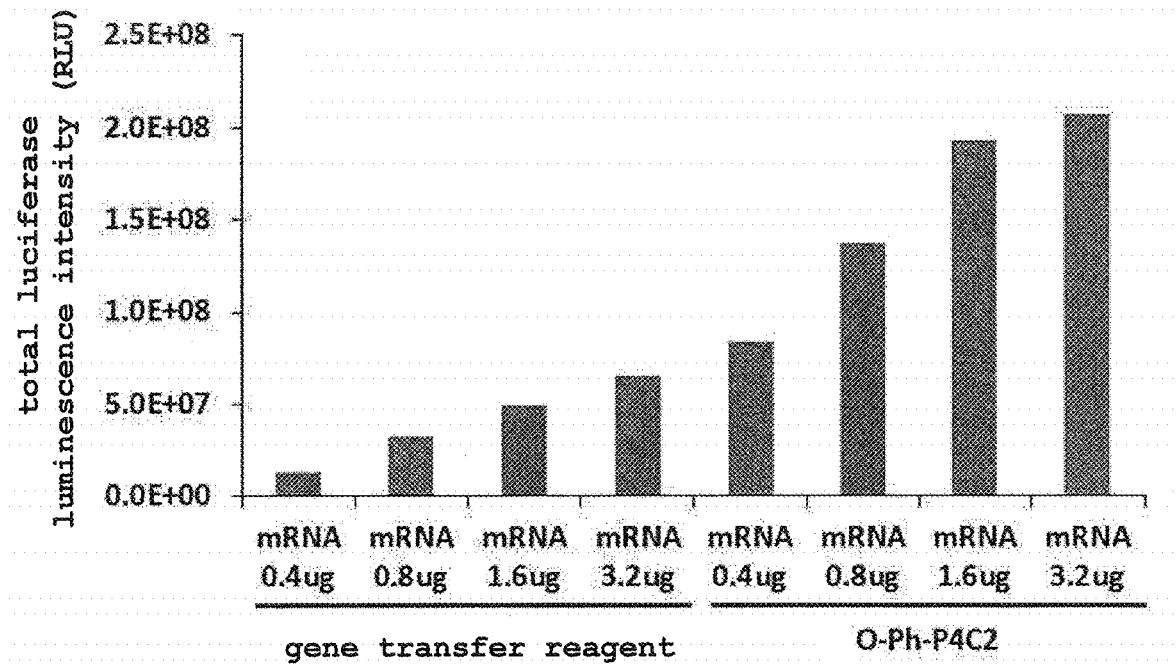
FIG. 9 shows the total amount of gene expression in vitro of LNP prepared from the cationic lipid of the present invention (O-Ph-P4C2) and gene transfer reagent (Lipofectamine MessengerMAX).

The results are shown in FIG. 9. LNP (O-Ph-P4C2_LNP) using the cationic lipid of the present invention showed superior gene expression activity at any mRNA amount as compared to gene transfer reagents.

[Experimental Example 15] Evaluation 5 of Gene Expression In Vitro

1. Preparation of LNP

LNP encapsulating mRNA that expresses EGFP (O-Ph-P4C2:DOPC:Chol:DMG-PEG2k=52.5:7.5:40:0.75) was prepared by a method similar to the method described in [Experimental Example 10], 1.

2. Preparation of Lipofectamine-mRNA Complex Using Gene Transfer Reagent

Lipofectamine-mRNA complex was prepared by the method described in [Experimental Example 14], 2.

3. Time-Course Evaluation of Gene Expression In Vitro

Jurkat cells which are human leukemia T cells were seeded in a 3.5 cm dish at $2.0 \times 10^5$ cells/2 mL/Dish 24 hr before transfection. After 24 hr, mRNA-encapsulated LNP solutions prepared at various concentrations were added by 80 μL (0.4, 0.8, 1.6, 3.2 μg as mRNA), or Lipofectamine-mRNA complex was added by 40, 80, 160, 320 μL (0.4, 0.8, 1.6, 3.2 μg as mRNA) to the 3.5 cm dish, and the mixture was cultured for 24 hr in an incubator. The culture medium was exchanged with FACS buffer (PBS containing 0.5% bovine serum albumin (BSA), 0.1% $NaN_3$), measurement was performed by a flow cytometer (NovoCyte; manufactured by ACEA Biosciences), and transgenic cells were analyzed.

4. Results

Figure 10:
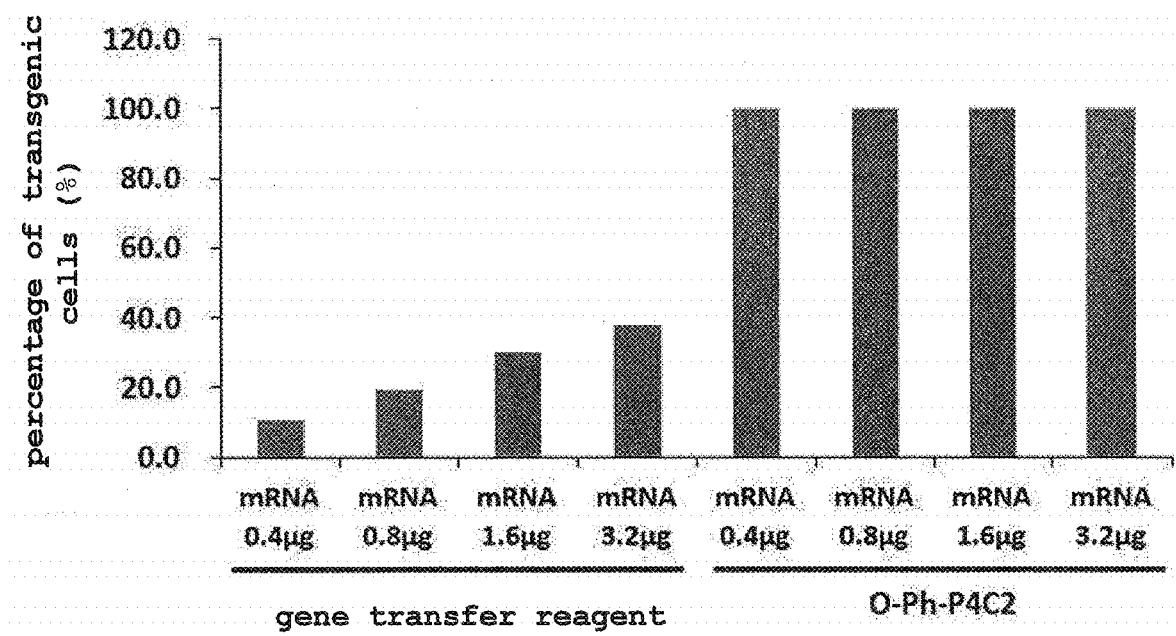
FIG. 10 shows the uniformity of gene expression in cells in vitro of LNP prepared from the cationic lipid of the present invention (O-Ph-P4C2) and a gene transfer reagent.

The results are shown in FIG. 10. A higher value shows that gene was introduced into many cells. With the gene transfer reagent, gene expression was observed only in some cells at any amount of mRNA, and the uniformity of expression was low. In contrast, it is clear that, in LNPs using the cationic lipid of the present invention, the gene was introduced into almost all cells regardless of the amount of mRNA, and the uniformity of expression was very high.

[Experimental Example 16] Evaluation of Gene Expression In Vivo (Subcutaneous Administration)

1. Preparation of Various LNPs

LNP encapsulating mRNA that expresses luciferase (cationic lipid:DOPE:Chol=60:30:10) was prepared by the method using micro flow path described in [Experimental Example 10].

2. Evaluation of Gene Knockdown Activity In Vivo

The prepared mRNA-encapsulated LNP was subcutaneously administered to the back of the neck of 6-week-old female C57/BL6J mice at 10 µL per 1 g body weight (0.05 mg/kg as dose of mRNA). After 5.5 hr from the administration, luciferin was intraperitoneally administered to the mice at 10 µL per 1 g body weight (1.5 g/kg as dose of luciferin). After 30 min, imaging was performed using IVIS imaging system. The average value of the luminance in the back of the neck of the mice was calculated as Photoms/sec from the acquired images, and used as an index of the gene expression activity in the back of the neck.

3. Results

Figure 11:
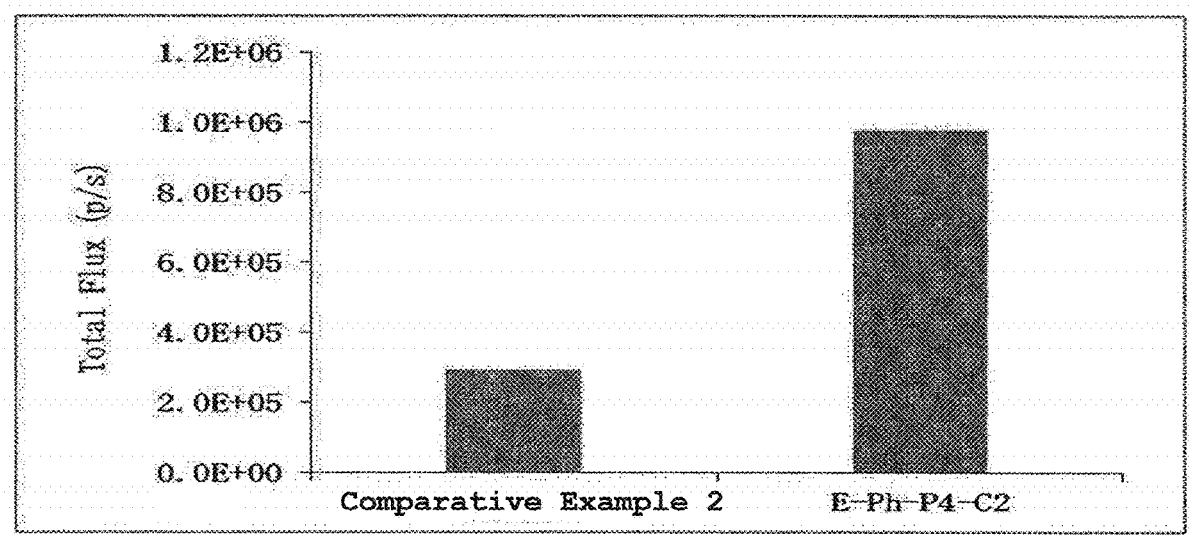
FIG. 11 shows the gene expression activity in vivo (subcutaneous) of various LNPs prepared from the cationic lipid of the present invention (E-Ph-P4C2) and Comparative Example 2.

The results are shown in FIG. 11. A higher value, i.e., higher total luciferase activity, means higher gene expression. LNP (E-Ph-P4C2_LNP) using the cationic lipid of the present invention showed higher gene expression activity in mouse (subcutaneous) than Comparative Example 2.

INDUSTRIAL APPLICABILITY

According to the present invention, since nucleic acid can be intracellularly introduced with high efficiency, it is useful for nucleic acid medicaments, gene therapy and biochemical experiments.

This application is based on patent application No. 2018-060764 filed in Japan, the contents of which are encompassed in full herein.

The invention claimed is:

1. A cationic lipid represented by the formula (1)

$$R^{3a}\underset{O}{\overset{O}{\|}}O-Z^a-Y^a-R^{2a}-X^a-R^{1a}-S$$
$$R^{3b}\underset{O}{\overset{O}{\|}}O-Z^b-Y^b-R^{2b}-X^b-R^{1b}-S$$ (1)

wherein in the formula (1),
  $R^{1a}$ and $R^{1b}$ are each independently an alkylene group having 1-6 carbon atoms,
  $X^a$ and $X^b$ are each independently a non-cyclic alkyl tertiary amino group having 1-6 carbon atoms and one tertiary amino group, or a cyclic alkylene tertiary amino group having 2-5 carbon atoms and 1-2 tertiary amino groups,
  $R^{2a}$ and $R^{2b}$ are each independently an alkylene group or an oxydialkylene group each having not more than 8 carbon atoms,
  $Y^a$ and $Y^b$ are each independently an ester bond, an amide bond, a carbamate bond, an ether bond or a urea bond, wherein $Z^a$ and $Z^b$ are each independently $Z^1$:

$$Z^1 = \left\{ \underset{(\phantom{)})_s}{\overset{(R^4)_u}{\phantom{X}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\right\}$$

wherein
  s is an integer of 0-3,
  t is an integer of 0-3,
  u is an integer of 0-4,
  $R^4$ in the number of u are each independently an acyl group having 2-4 carbon atoms, an alkoxycarbonyl group having 2-4 carbon atoms, a carbamoyl group having 2-4 carbon atoms, an acyloxy group having 2-4 carbon atoms, an acylamino group having 2-4 carbon atoms, an alkoxycarbonylamino group having 2-4 carbon atoms, a fluorine atom, a chlorine atom, a bromine atom, a iodine atom, an alkylsulfanyl group having 1-4 carbon atoms, an alkylsulfonyl group having 1-4 carbon atoms, an arylsulfonyl group having 6-10 carbon atoms, a nitro group, a trifluoromethyl group, a cyano group, an alkyl group having 1-4 carbon atoms, a ureido group having 1-4 carbon atoms, an alkoxy group having 1-4 carbon atoms, an aryl group having 6-10 carbon atoms, or an aryloxy group having 6-10 carbon atoms, and
  $R^{3a}$ and $R^{3b}$ are each independently
    a residue derived from a reaction product of (a) a liposoluble vitamin having a hydroxyl group selected from the group consisting of retinol, ergosterol, 7-dehydrocholesterol, calciferol, cholecalciferol, dihydroergocalciferol, dihydrotachysterol, tocopherol, and tocotrienol, and (b) succinic anhydride or glutaric anhydride, or
    a residue derived from a reaction product of (a) a sterol derivative having a hydroxyl group selected from the group consisting of cholesterol, cholestanol, stigmasterol, β-sitosterol, lanosterol, and ergosterol, and (b) succinic anhydride or glutaric anhydride, or
    an aliphatic hydrocarbon group having 12-22 carbon atoms selected from the group consisting of tridecyl group, pentadecyl group, heptadecyl group, nonadecyl group, heptadecenyl group, heptadecadienyl group, and 1-hexylnonyl group.

2. The cationic lipid according to claim 1, wherein s is 0.

3. The cationic lipid according to claim 1, wherein $X^a$ and $X^b$ are each independently a cyclic alkylene tertiary amino group having 2-5 carbon atoms and 1-2 tertiary amino groups.

4. The cationic lipid according to claim 1, wherein $R^{3a}$ and $R^{3b}$ are each independently a residue derived from a reaction product of (a) a sterol derivative having a hydroxyl group selected from the group consisting of cholesterol, cholestanol, stigmasterol, β-sitosterol, lanosterol, and ergosterol, and (b) succinic anhydride or glutaric anhydride.

5. The cationic lipid according to claim 1, wherein $R^{3a}$ and $R^{3b}$ are each independently a residue derived from a reaction product of (a) a liposoluble vitamin having a hydroxyl group selected from the group consisting of retinol, ergosterol, 7-dehydrocholesterol, calciferol, cholecalciferol, dihydroergocalciferol, dihydrotachysterol, tocopherol, and tocotrienol, and (b) succinic anhydride or glutaric anhydride.

6. The cationic lipid according to claim 1, wherein $R^{3a}$ and $R^{3b}$ are each independently an aliphatic hydrocarbon group having 12-22 carbon atoms selected from the group consisting of tridecyl group, pentadecyl group, heptadecyl group, nonadecyl group, heptadecenyl group, heptadecadienyl group, and 1-hexylnonyl group.

7. A lipid membrane structure comprising the cationic lipid according to claim 1 as a constituent lipid of the membrane.

8. A nucleic acid-introducing agent comprising the cationic lipid according to claim 1.

9. A method for introducing a nucleic acid into a cell in vitro, comprising bringing the nucleic acid-introducing agent according to claim 8 encapsulating the nucleic acid into contact with the cell.

10. A method for introducing a nucleic acid into a target cell, comprising administering the nucleic acid-introducing agent according to claim 8 encapsulating the nucleic acid to a living organism to allow for delivery of the nucleic acid to the cell.

11. The cationic lipid according to claim 2, wherein $X^a$ and $X^b$ are each independently a cyclic alkylene tertiary amino group having 2-5 carbon atoms and 1-2 tertiary amino groups.

12. The cationic lipid according to claim 11, wherein $R^{3a}$ and $R^{3b}$ are each independently a residue derived from a reaction product of (a) a sterol derivative having a hydroxyl group selected from the group consisting of cholesterol, cholestanol, stigmasterol, β-sitosterol, lanosterol, and ergosterol, and (b) succinic anhydride or glutaric anhydride.

13. The cationic lipid according to claim 11, wherein $R^{3a}$ and $R^{3b}$ are each independently a residue derived from a reaction product of (a) a liposoluble vitamin having a hydroxyl group selected from the group consisting of retinol, ergosterol, 7-dehydrocholesterol, calciferol, cholecalciferol, dihydroergocalciferol, dihydrotachysterol, tocopherol, and tocotrienol, and (b) succinic anhydride or glutaric anhydride.

14. The cationic lipid according to claim 11, wherein $R^{3a}$ and $R^{3b}$ are each independently an aliphatic hydrocarbon group having 12-22 carbon atoms selected from the group consisting of tridecyl group, pentadecyl group, heptadecyl group, nonadecyl group, heptadecenyl group, heptadecadienyl group, and 1-hexylnonyl group.

15. A nucleic acid-introducing agent, comprising the lipid membrane structure according to claim 7.

16. A method for introducing a nucleic acid into a cell in vitro, comprising bringing the nucleic acid-introducing agent according to claim 15 encapsulating the nucleic acid into contact with the cell.

17. A method for introducing a nucleic acid into a target cell, comprising administering the nucleic acid-introducing agent according to claim 15 encapsulating the nucleic acid to a living organism to allow for delivery of the nucleic acid to the cell.

* * * * *